US009489738B2

(12) United States Patent
Daon et al.

(10) Patent No.: US 9,489,738 B2
(45) Date of Patent: *Nov. 8, 2016

(54) SYSTEM AND METHOD FOR TRACKING NON-VISIBLE STRUCTURE OF A BODY WITH MULTI-ELEMENT FIDUCIAL

(71) Applicant: Navigate Surgical Technologies, Inc., Vancouver (CA)

(72) Inventors: Ehud (Udi) Daon, North Vancouver (CA); Martin Gregory Beckett, Bowen Island (CA)

(73) Assignee: Navigate Surgical Technologies, Inc., Vancouver, BC (CA)

( * ) Notice: Subject to any disclaimer, the term of this patent is extended or adjusted under 35 U.S.C. 154(b) by 331 days.

This patent is subject to a terminal disclaimer.

(21) Appl. No.: 14/257,024

(22) Filed: Apr. 21, 2014

(65) Prior Publication Data
US 2014/0320600 A1    Oct. 30, 2014

Related U.S. Application Data

(60) Provisional application No. 61/816,283, filed on Apr. 26, 2013.

(51) Int. Cl.
*H04N 13/00* (2006.01)
*G06T 7/00* (2006.01)
(Continued)

(52) U.S. Cl.
CPC ............. *G06T 7/0044* (2013.01); *A61B 34/20* (2016.02); *A61B 90/39* (2016.02); *A61C 1/082* (2013.01);
(Continued)

(58) Field of Classification Search
USPC ........................................................ 348/45
See application file for complete search history.

(56) References Cited

U.S. PATENT DOCUMENTS 5,230,623 A    7/1993    Guthrie
5,438,991 A    8/1995    Yu et al.
(Continued)

FOREIGN PATENT DOCUMENTS

DE    10 2005 026654    12/2006
DE          2009009158       9/2010
(Continued)

OTHER PUBLICATIONS

European Patent Office, International Search Report, International Application No. PCT/EP2013/073401, Navigate Surgical Technologies, Inc., Mar. 19, 2014.
(Continued)

*Primary Examiner* — Leron Beck
(74) *Attorney, Agent, or Firm* — Kevin R. Erdman; Brannon Sowers & Cracraft PC

(57) ABSTRACT

A monitoring system tracks the non-visible structure of a body in three dimensions. A tracker obtains image information of the object and instruments in its vicinity, all bearing 3D tracking markers. A controller spatially relates image information with previously obtained scan data of the object revealing non-visible structure of the object. For the scan a fiducial reference detectable in the scan is removably attached to a location on the object. The scan data and image information is used by the controller to provide the user with real time information on the relative 3D locations and orientations of instruments and non-visible structure of the body. In a further embodiment the monitoring system may be used to model and track changes in the body itself. In other embodiments, a model of the body and instruments is used to track contemplated actions and warn about possibly inappropriate instrument procedures.

31 Claims, 16 Drawing Sheets

(51) Int. Cl.
*H04N 13/02* (2006.01)
*A61C 1/08* (2006.01)

(52) U.S. Cl.
CPC ....... *H04N 13/02* (2013.01); *A61B 2034/2055* (2016.02); *A61B 2034/2065* (2016.02); *A61B 2090/363* (2016.02); *A61B 2090/364* (2016.02); *A61B 2090/3937* (2016.02); *A61B 2090/3966* (2016.02); *A61B 2090/3983* (2016.02); *A61B 2090/3991* (2016.02)

(56) References Cited

U.S. PATENT DOCUMENTS

| | | | |
|---|---|---|---|
| 5,603,318 | A | 2/1997 | Heilbrun et al. |
| 5,828,770 | A | 10/1998 | Leis et al. |
| 5,967,777 | A | 10/1999 | Klein |
| 6,122,541 | A | 9/2000 | Cosman et al. |
| 6,468,265 | B1 | 10/2002 | Evans et al. |
| 6,529,765 | B1 | 3/2003 | Franck et al. |
| 7,653,455 | B2 | 1/2010 | Cinador |
| 7,720,521 | B2 | 5/2010 | Chang |
| 7,758,345 | B1 | 7/2010 | Christensen |
| 7,894,878 | B2 | 2/2011 | Noujeim |
| 7,899,512 | B2 | 3/2011 | Labadie |
| 8,172,573 | B2 | 5/2012 | Sonenfeld |
| 2004/0002642 | A1 | 1/2004 | Dekel et al. |
| 2004/0097952 | A1 | 5/2004 | Sarin et al. |
| 2004/0138556 | A1* | 7/2004 | Cosman ............ G06T 3/00 600/424 |
| 2005/0085719 | A1 | 4/2005 | Franklin et al. |
| 2005/0163342 | A1 | 7/2005 | Persky |
| 2005/0182318 | A1 | 8/2005 | Kaji et al. |
| 2006/0142657 | A1 | 6/2006 | Quaid et al. |
| 2006/0165310 | A1 | 7/2006 | Mack |
| 2006/0212044 | A1 | 9/2006 | Bova et al. |
| 2006/0247517 | A1 | 11/2006 | Labadie et al. |
| 2006/0281991 | A1* | 12/2006 | Fitzpatrick ......... A61B 90/16 600/426 |
| 2007/0208252 | A1 | 9/2007 | Makower |
| 2007/0223910 | A1 | 9/2007 | Aoki |
| 2007/0253541 | A1 | 11/2007 | Sukovic et al. |
| 2008/0026338 | A1 | 1/2008 | Cinader |
| 2008/0135733 | A1 | 6/2008 | Feilkas |
| 2008/0161682 | A1 | 7/2008 | Kendrick et al. |
| 2008/0171305 | A1 | 7/2008 | Sonenfeld et al. |
| 2008/0183071 | A1 | 7/2008 | Strommer |
| 2008/0193896 | A1* | 8/2008 | Yang ............. A61C 13/0027 433/68 |
| 2008/0200927 | A1 | 8/2008 | Hartmann et al. |
| 2008/0262345 | A1* | 10/2008 | Fichtinger ........ A61B 6/504 600/426 |
| 2008/0319491 | A1 | 12/2008 | Schoenefeld |
| 2009/0012509 | A1 | 1/2009 | Csavoy |
| 2009/0171196 | A1 | 7/2009 | Olson et al. |
| 2009/0253095 | A1 | 10/2009 | Salcedo |
| 2010/0039506 | A1* | 2/2010 | Sarvestani ............ 348/65 |
| 2010/0049195 | A1 | 2/2010 | Park et al. |
| 2010/0168562 | A1 | 7/2010 | Zhao et al. |
| 2010/0168763 | A1 | 7/2010 | Zhao et al. |
| 2010/0210939 | A1 | 8/2010 | Hartmann et al. |
| 2010/0217139 | A1 | 8/2010 | Pinter et al. |
| 2010/0298712 | A1 | 11/2010 | Pelissier et al. |
| 2011/0008751 | A1 | 1/2011 | Patterssen |
| 2011/0087332 | A1* | 4/2011 | Bojarski ............ A61B 17/155 623/20.32 |
| 2011/0217667 | A1 | 9/2011 | Groscurth |
| 2011/0257653 | A1 | 10/2011 | Hughes |
| 2012/0065496 | A1 | 3/2012 | Stratton |
| 2012/0115107 | A1 | 5/2012 | Adams |
| 2012/0259204 | A1 | 10/2012 | Carrat et al. |
| 2012/0265051 | A1 | 10/2012 | Fischer et al. |
| 2012/0283637 | A1 | 11/2012 | Cohen |
| 2013/0063558 | A1 | 3/2013 | Phipps |
| 2013/0258353 | A1 | 10/2013 | Kosmecki et al. |
| 2014/0030669 | A1 | 1/2014 | Hey et al. |
| 2014/0049629 | A1* | 2/2014 | Siewerdsen ........ A61B 19/5244 348/77 |

FOREIGN PATENT DOCUMENTS

| | | |
|---|---|---|
| DE | 102009009158 | 9/2010 |
| DE | 2010042540 | 4/2012 |
| DE | 2011012460.8 | 8/2012 |
| EP | 1527417 | 9/2011 |
| FR | 2 929 794 | 10/2009 |
| GB | 2 416 949 | 2/2006 |
| JP | 2000046546 | 2/2000 |
| JP | 2007253748 | 10/2007 |
| JP | 2009172411 | 5/2009 |
| WO | 99/27839 | 6/1999 |
| WO | 02/076302 | 10/2002 |
| WO | 2008/009136 | 1/2008 |
| WO | 2010/086374 | 5/2010 |
| WO | 2011109041 | 9/2011 |
| WO | 2011113441 | 9/2011 |
| WO | 2013144939 | 4/2012 |
| WO | 2012068679 | 5/2012 |
| WO | 2012095642 | 7/2012 |
| WO | 2012/149548 | 11/2012 |
| WO | 2012149548 | 11/2012 |
| WO | 2013096766 | 6/2013 |
| WO | 2011/109041 | 10/2013 |
| WO | 2013144208 | 10/2013 |

OTHER PUBLICATIONS

European Patent Office, Written Opinion of the International Searching Authority, International Application No. PCT/EP2013/073401, Navigate Surgical Technologies, Inc., Mar. 19, 2014.
European Patent Office, Written Opinion of the International Searching Authority, International Application No. PCT/IL2015/050400, Navigate Surgical Technologies, Inc., Jul. 16, 2015.
European Patent Office, International Search Report, International Application No. PCT/IL2015/050400, Navigate Surgical Technologies, Inc., Jul. 16, 2015.
USPTO, Non-Final Office Action for U.S. Appl. No. 13/744,967, dated Jun. 30, 2015.
USPTO, Non-Final Office Action for U.S. Appl. No. 13/745,249, dated Jun. 30, 2015.
USPTO, Final Office Action for U.S. Appl. No. 13/745,763, dated Jul. 8, 2015.
Arizona Center for Laser Dentistry, Root Canals at the Arizona Center for Laser Dentistry, Captured via web.archive.org on Dec. 19, 2010, retrieved Jun. 2, 2015.
European Patent Office, International Written Opinion, dated Sep. 29, 2014 (PCT/IB2014/060403).
European Patent Office, International Written Opinion, dated Oct. 17, 2014 (PCT/EP2014/067280).
European Patent Office, International Search Report, dated Jul. 17, 2014 (PCT/EP2014/058406).
European Patent Office, International Written Opinion, dated Aug. 18, 2014 (PCT/EP2014/058406).
European Patent Office, International Written Opinion, dated Jul. 30, 2014 (PCT/EP2014/057656).
European Patent Office, International Written Opinion, dated Jul. 30, 2014 (PCT/EP2014/060018).
International Search Report and Written Opinion for PCT/EP2014/067279, dated Nov. 10, 2014.
International Search Report and Written Opinion for PCT/EP2014/067280, dated Oct. 27, 2014.
Office Action in related U.S. Appl. No. 13/735,487 dated Nov. 14, 2014.
Office Action in related U.S. Appl. No. 13/745,763 dated Dec. 29, 2014.
USPTO, Non-Final Office Action for U.S. Appl. No. 13/822,358, dated Feb. 13, 2015.

(56) References Cited

OTHER PUBLICATIONS

USPTO, Response to Non-Final Office Action for U.S. Appl. No. 13/745,763, dated Mar. 25, 2015.
Japanese Patent Office (JPO) Notice of Preliminary Rejection,Japan Patent Application No. 2014-537811, Based upon PCT/IL2012/000363, Jan. 25, 2016, which claims priority to U.S. Appl. No. 13/571,284, now U.S. Pat. No. 8,938,282.
Japanese Patent Office (JPO) Notice of Preliminary Rejection,Japanese Patent Application No. 2015-541159, Based upon PCT/EP2013/0073401, Mar. 1, 2016, which claims priority to U.S. Appl. No. 14/156,269, now U.S. Pat. No. 8,908,918.
International Searching Authority, International Search Report, dated Sep. 3, 2013 (PCT/IL2013/000032).
International Searching Authority, International Written Opinion, dated Sep. 3, 2013 (PCT/IL2013/000032).
International Searching Authority, International Search Report, dated Sep. 16, 2013 (PCT/EP2013/056525).
International Searching Authority, International Search Report, mailed Sep. 17, 2013 (PCT/IL2013/000031).
Prosecution of U.S. Appl. No. 13/571,284, from First Office Action of Aug. 15, 2013 to Amendment with Request for Continued Examination of Feb. 26, 2014.
International Searching Authority, International Search Report, mailed Mar. 4, 2013 (PCT/IL2012/000363).
International Searching Authority, International Written Opinion, mailed Mar. 4, 2013 (PCT/IL2012/000363).
International Searching Authority, International Search Report, dated Feb. 18, 2014 (PCT/EP2013/073416).
International Searching Authority, International Written Opinion, dated Feb. 18, 2014 (PCT/EP2013/073416).

* cited by examiner

SYSTEM AND METHOD FOR TRACKING NON-VISIBLE STRUCTURE OF A BODY WITH MULTI-ELEMENT FIDUCIAL

CROSS-REFERENCE TO RELATED APPLICATIONS

The present application claims priority under 35 U.S.C. §119(e) of U.S. Patent Provisional Application Ser. No. 61/816,283, filed Apr. 26, 2013, the disclosures of which are incorporated by reference herein.

BACKGROUND OF THE INVENTION

1. Field of the Invention

The invention relates to location monitoring hardware and software systems. More specifically, the field of the invention is that of tracking in three-dimensions the position and orientation of the internal or otherwise non-visible structure of a body.

2. Description of the Related Art

Visual and other sensory systems are known, with such systems being capable of both observing and monitoring surgical procedures. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

In a first aspect of the invention a system for monitoring the position and orientation of non-visible structure of a body comprises (1) a fiducial reference adapted to be rigidly attached to the body; (2) a three-dimensional tracking marker rigidly attached at a predetermined location in a predetermined orientation on an implement proximate the body; (3) a tracker arranged to obtain image information about an area encompassing the fiducial reference and the marker; (4) a computer system coupled to the tracker and having a previously obtained scan data of the body with the fiducial reference fixed to the body and including a processor with memory and a software program having a series of instructions for execution by the processor to determine the relative position and orientation of the marker and the fiducial reference based on the image information and the scan data scan data; (5) and a display system in communication with the computer system; wherein the system is characterized by at least one of the marker and the tracker being connected to the fiducial reference in a fixed relative position and orientation.

In another embodiment the system for monitoring the position and orientation of non-visible structure of a body may comprise (1) a fiducial reference capable of being attached to the body, the fiducial reference being perceptible in scan data of the body; (2) a three-dimensional tracking marker having a fixed connection with the fiducial reference; (3) a tracker having sensory equipment for obtaining image information of a region encompassing the tracking marker; (4) a computing device in communication with the tracker, the computing device having software capable of recognizing the fiducial reference in the scan data and in the image information and calculating a model of the region based on the scan data, the identity of the fiducial reference, and the image information.

In another embodiment the system for monitoring the position and orientation of non-visible structure of a body may comprise (1) a tracker for obtaining image information of an area encompassing the body; (2) a fiducial reference configured for removably attaching to the body to be observable by the tracker; (3) a controller configured to spatially relate the image information to previously obtained scan data of the body with the fiducial reference attached to the body; and (3) software executable by the controller to determine a three-dimensional location and orientation of the fiducial reference by relating the image information to the scan data. The fiducial reference may be marked or shaped for having its location or its orientation or both determined from the scan data. The fiducial reference may be marked or shaped to be uniquely identified from the scan data.

A tracking marker may be in a fixed three-dimensional spatial relationship with the fiducial reference, and the tracking marker may be configured for having its location or its orientation or both determined by the controller based on the image information and the scan data. The tracking marker may be configured to be removably and rigidly connected to the fiducial reference by a first tracking pole. The first tracking pole may be a three-dimensional structure uniquely identifiable by the controller from the image information. The first tracking pole may have a three-dimensional structure allowing for the three-dimensional orientation of the tracking pole to be determined by the controller from image information. The first tracking pole and fiducial reference may be configured to allow the first tracking pole to connect to a single unique location on the fiducial reference in a first single unique three-dimensional orientation. The fiducial reference may be configured for the attachment in a single second unique three-dimensional orientation of at least a second tracking pole attached to a second tracking marker. The tracking marker may have a three-dimensional shape uniquely identifiable by the controller from image information. The tracking marker may have a three-dimensional shape that allows the three-dimensional orientation of the tracking marker to be determined by the controller from image information. The tracking marker may have a marking uniquely identifiable by the controller and the marking is configured for allowing at least one of its location and its orientation to be determined by the controller based on the image information and the scan data.

In another embodiment of the system for monitoring the position and orientation of non-visible structure of a body the fiducial reference comprises a multi-element fiducial pattern. The pattern comprises a plurality of pattern segments and every segment is individually configured for having a segmental three-dimensional location and orientation determinable based on scan data of the surgical site, and for having the segmental three-dimensional location and orientation determinable based on image information about the surgical site. The plurality of pattern segments may have unique differentiable shapes that allow the controller to identify them uniquely from at least one of scan data and image information. The system may further comprise three-dimensional tracking markers attached to at least a selection of the pattern segments, and the tracking markers may have at least one of identifying marks and orientation marks that allow their three-dimensional orientations to be determined by the controller from the image information. The controller may be configured for determining the locations and orientations of at least a selection of the pattern segments based on image information and scan data. The controller may be configured for calculating the locations of anatomical features in the proximity of the multi-element fiducial pattern.

The system may comprising further tracking markers attached to implements proximate the surgery site, and the controller may be configured for determining locations and orientations of the implements based on image information and information about the further tracking markers. The fiducial reference may be rigidly and removably attachable to the body. The fiducial reference may be repeatably attachable in the same three-dimensional orientation to the body.

In another aspect of the invention a method for relating in real time the three-dimensional position and orientation of non-visible structure of a body to the location and orientation of the structure in a scan of the body comprises (1) removably attaching a fiducial reference to a fiducial location on the body; (2) performing a scan with the fiducial reference attached to the fiducial location to obtain scan data; (3) determining the three-dimensional location and orientation of the fiducial reference from the scan data; (4) obtaining real time image information of the body; (5) determining in real time the three-dimensional location and orientation of the fiducial reference from the image information; and (6) deriving a spatial transformation matrix for expressing in real time the three-dimensional location and orientation of the fiducial reference as determined from the image information in terms of the three-dimensional location and orientation of the fiducial reference as determined from the scan data. Obtaining real time image information of the surgical site may comprise rigidly and removably attaching to the fiducial reference a first tracking marker in a fixed three-dimensional spatial relationship with the fiducial reference. The first tracking marker may be configured for having its location and its orientation determined based on image information. The attaching the first tracking marker to the fiducial reference may comprise rigidly and removably attaching the first tracking marker to the fiducial reference by means of a tracking pole.

The fiducial reference may be a multi-element fiducial pattern comprising a plurality of pattern segments individually locatable based on the scan data and the method may further comprise determining the three-dimensional location and orientation of the fiducial reference from scan data comprises determining the three-dimensional location and orientation of at least a selection of the plurality of pattern segments from the scan data; and determining in real time the three-dimensional location and orientation of the fiducial reference from the image information comprises determining the three-dimensional location and orientation of the at least a selection of the plurality of pattern segments from image information.

In another embodiment a method for tracking in real time changes in a body comprises (1) removably attaching a multi-element fiducial reference to a fiducial location on the body, the multi-element fiducial reference comprising a plurality of pattern segments individually locatable based on scan data; (2) performing a scan with the fiducial reference attached to the fiducial location to obtain the scan data; (3) determining the three-dimensional locations and orientations of at least a selection of the pattern segments based on the scan data; (3) obtaining real time image information of a region encompassing the multi-element fiducial reference; (4) determining in real time the three-dimensional locations and orientations of the at least a selection of the pattern segments from the image information; and (5) deriving in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data.

In another embodiment a method for real time monitoring the three-dimensional position and orientation of an object in relation to a body comprises: (1) removably attaching a fiducial reference to a fiducial location on the body; (2) performing a scan with the fiducial reference attached to a fiducial location to obtain scan data; (3) determining the three-dimensional location and orientation of the fiducial reference from the scan data; (4) obtaining real time image information of a region encompassing the fiducial reference and the object; (5) determining in real time the three-dimensional location and orientation of the fiducial reference from the image information; (6) deriving a spatial transformation matrix for expressing in real time the three-dimensional location and orientation of the fiducial reference as determined from image information in terms of the three-dimensional location and orientation of the fiducial reference as determined from scan data; (7) determining in real time the three-dimensional location and orientation of the object from the image information; and (8) relating the three-dimensional location and orientation of the object to the three-dimensional location and orientation of the fiducial reference as determined from the image information. The determining in real time the three-dimensional location and orientation of the object from the image information may comprise rigidly attaching a tracking marker to the object. The method may further comprise determining in real time the position and orientation of the object relative to the position and orientation of non-visible structure of the body revealed in the scan.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
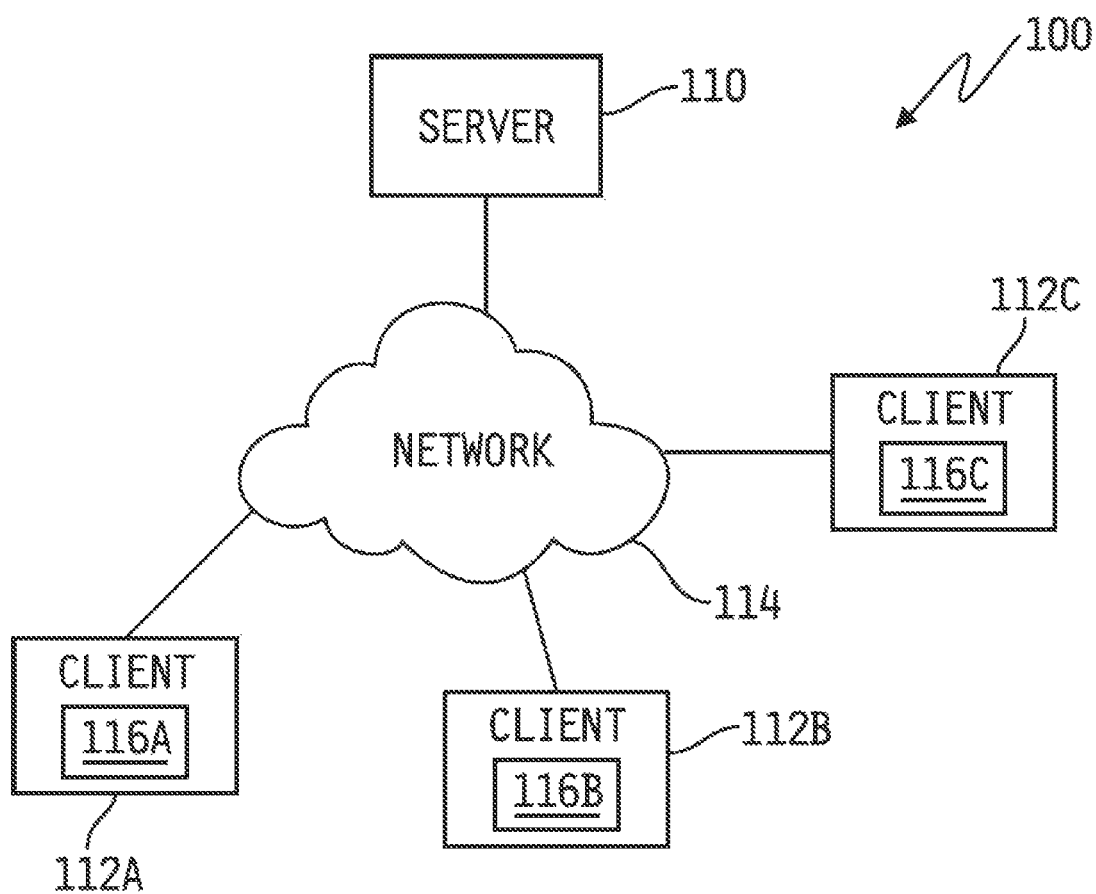
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions that follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer.

The algorithms presented herein are not inherently related to any particular computer or other apparatus unless explicitly indicated as requiring particular hardware. In some cases, the computer programs may communicate or relate to other programs or equipments through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience; therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user.

Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data ("CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "body", "non-visible structure", "scan," "fiducial reference", "fiducial location", "marker," "tracker" and "image information" have particular meanings in the present disclosure. For purposes of the present disclosure, the term "body" and derivatives thereof refer to a human body or part thereof, as well as to an object having internal and external structure. The term "non-visible structure" refers to structure that is not visible by virtue of being inside a body, or by virtue of being made evident only by means of stimulus or radiation other than visible radiation, or by virtue of a line of sight to the structure not being sufficiently maintainable, such as when there are obscuring features blocking the view. The term "scan" or derivatives thereof refer to x-ray, magnetic resonance imaging (MRI), computerized tomography (CT), sonography, cone beam computerized tomography (CBCT), or any system that produces a quantitative spatial representation of a patient or object. The term "fiducial reference" or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site or on an object to be monitored. The term "marker" or "tracking marker" refers to an object or reference that may be perceived by a sensor proximate to the location of the surgical or dental procedure or on an object to be monitored, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. In some embodiments, the tracker may be a non-stereo optical tracker, for example a camera. The camera may, for example, operate in the visible or near-infrared range. The term "image information" is used in the present specification to describe information obtained by the tracker, whether optical or otherwise, and usable for determining the location of the markers and their orientation and movement continually in 'real time' during a procedure.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
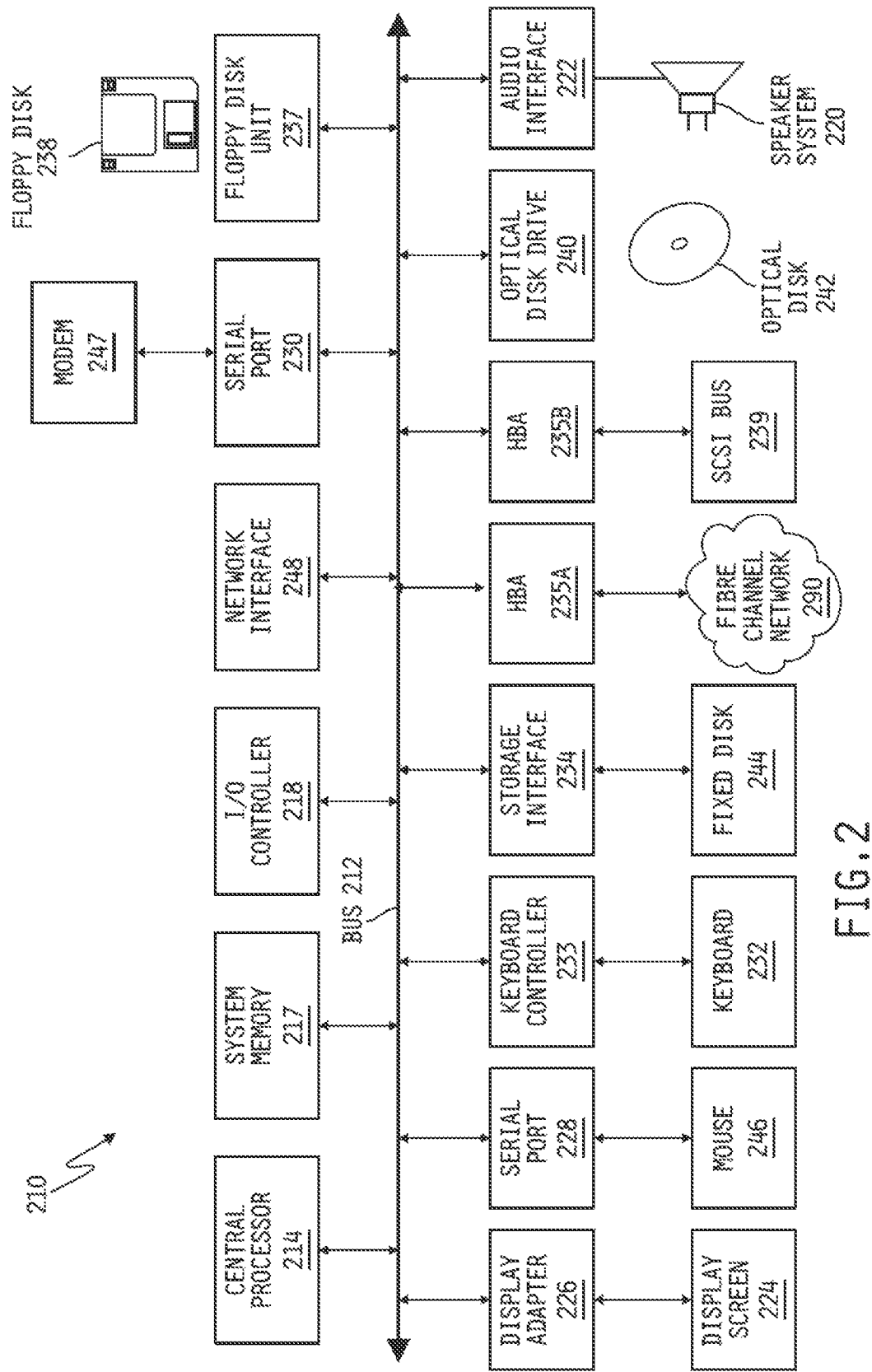
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized as controller and display in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS), which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an Internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on), including the hardware components of FIGS. 3A-I, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The present invention relates to embodiments of surgical hardware and software monitoring systems and methods for tracking the three-dimensional location and orientation of the structure of a body, the body being an object or a medical or dental patient, and thus surgical planning while the patient is available for surgery is possible, for example while the patient is being prepared for surgery so the system may model the surgical site. This is achieved by mapping onto scan data, obtained from a scan of the body with a fiducial key or marker attached in or on the body, image information obtained from a tracker monitoring the body. In the particular case of surgical application, the present invention relates to a surgical hardware and software monitoring system and method which allows for surgical planning while the patient is available for surgery, for example while the patient is being prepared for surgery so that the system may model the surgical site. While the invention applies to any body, object or artifact capable of having its internal or other non-visible structure revealed by scan techniques employing penetrating stimulus or radiation, we shall make extensive use of medical examples to clarify the invention. The invention, however, is equally applicable to a diverse collection of fields where the three-dimensional location and orientation of internal structure or other non-readily observable structure, such as complex folded exterior structures, has to be to be monitored and tracked. Examples abound in different forensic fields, failure analysis, manufacture, quality control, archaeology, paleontology, as well as in the design and development of complex mechanical structures, such as, for example, structures with complex internal ducting. X-ray techniques have been used in these fields for some decades and newer scan techniques are finding ever-increasing application, thereby making the present invention increasingly useful in such those fields.

Figure 3A:
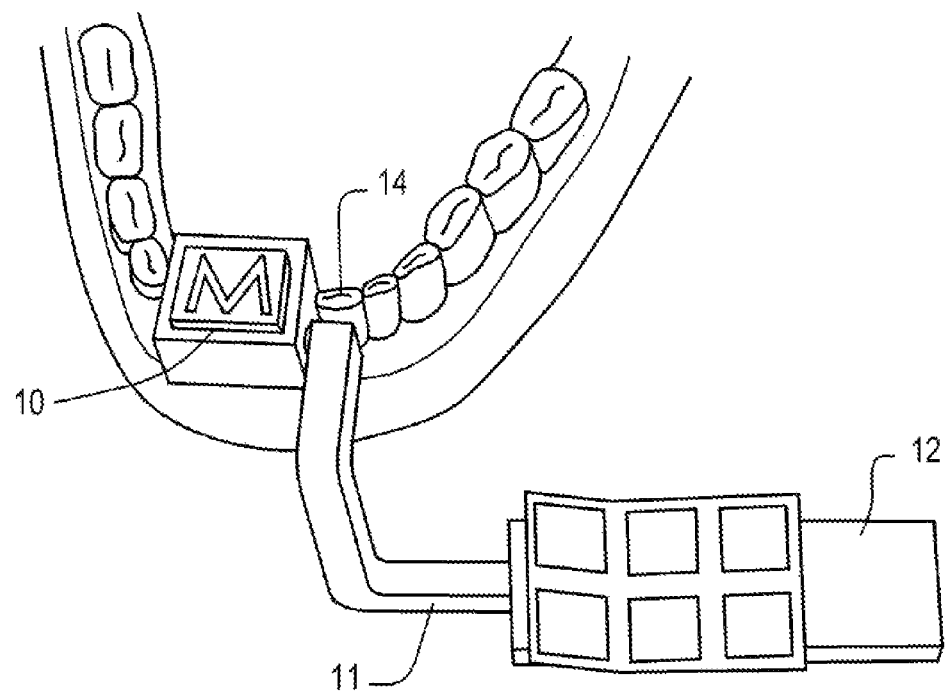
FIGS. 3A-J are drawings of hardware components of the surgical monitoring system according to embodiments of the invention.
Figure 3B:
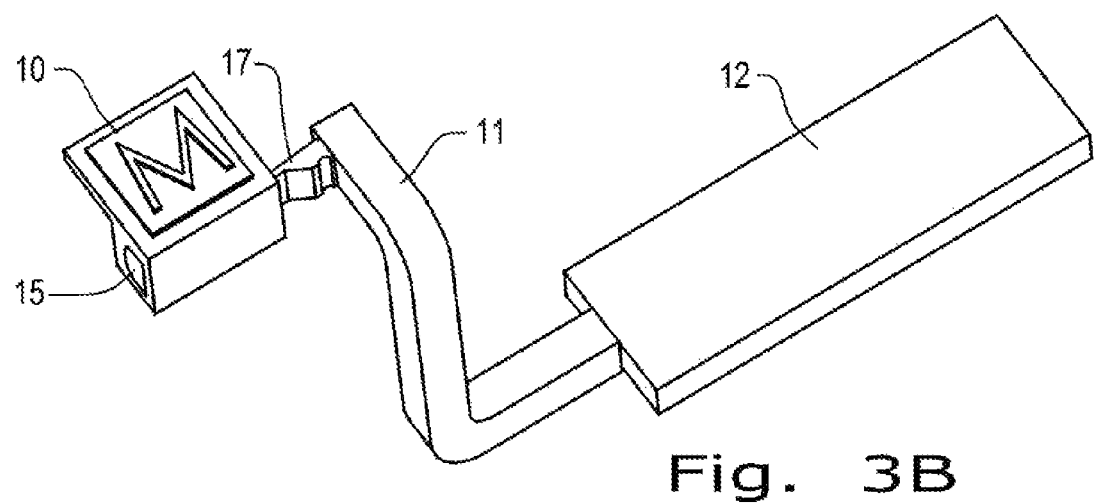
Figure 3C:
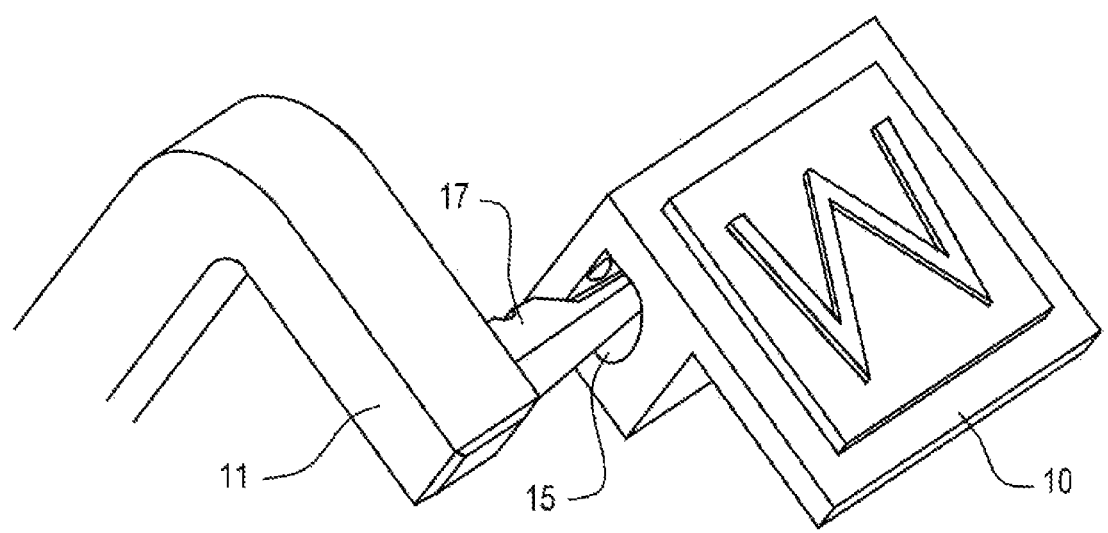
Figure 3D:
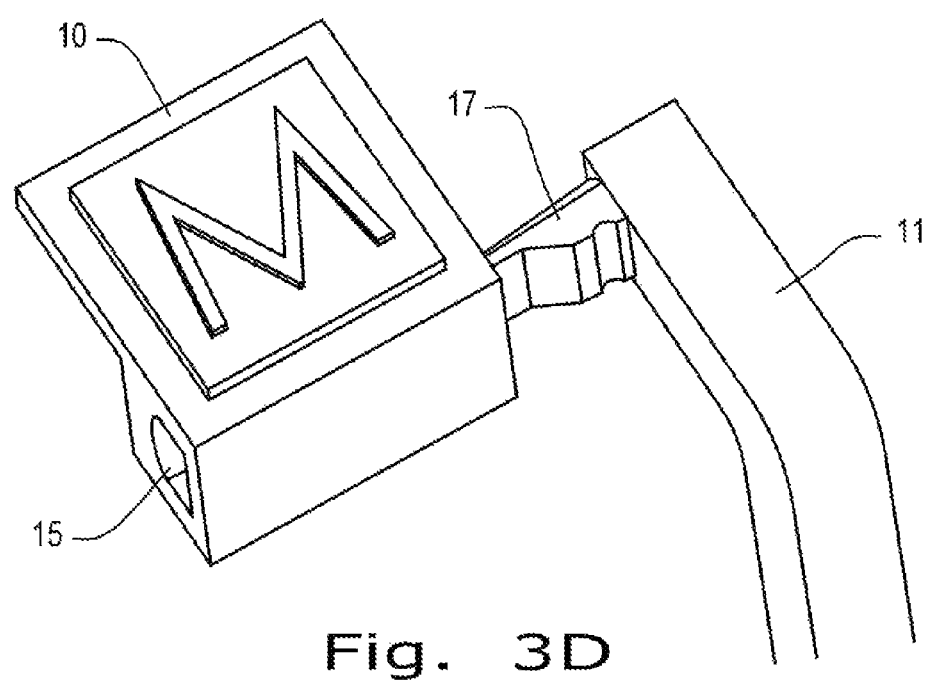
Figure 3E:
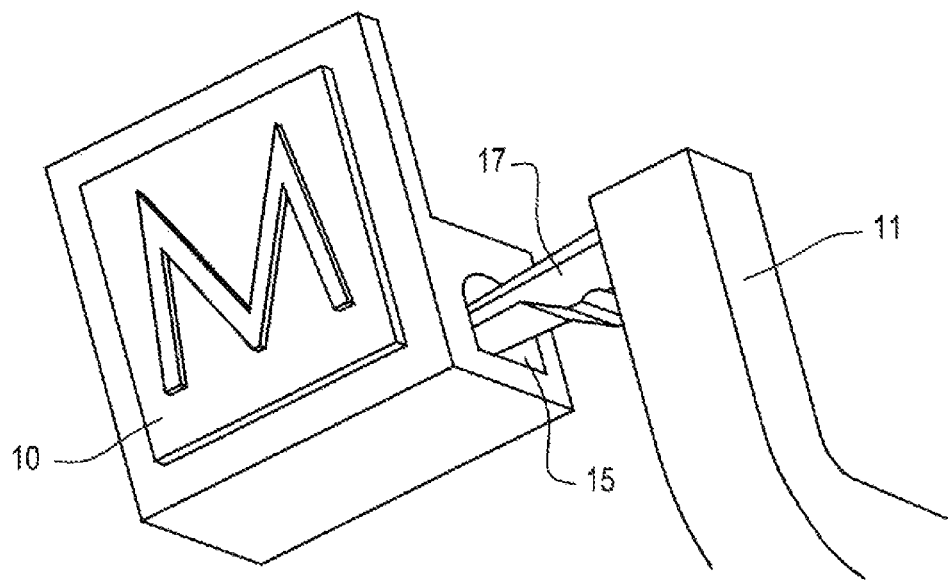
Figure 3F:
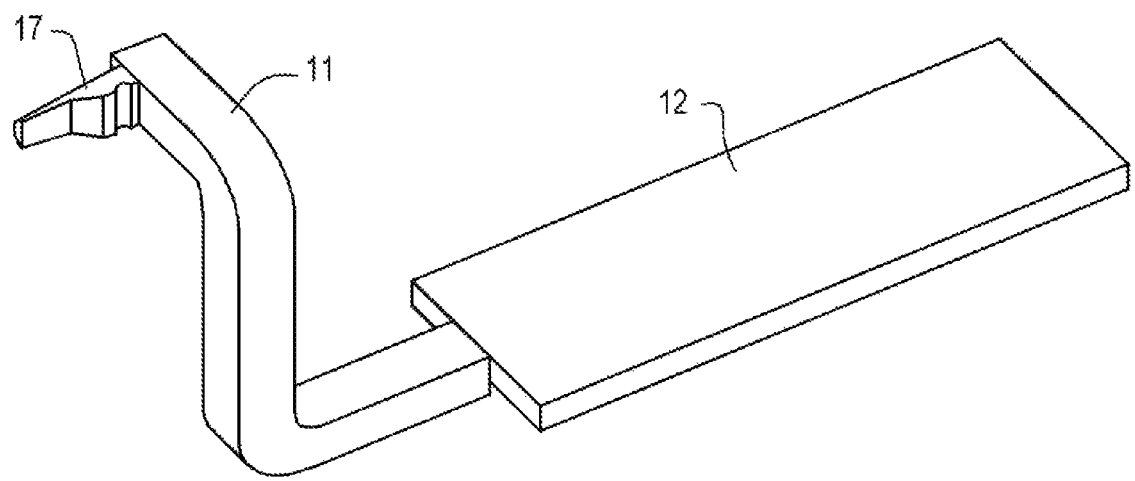

Focusing now on examples from the medical field, the system uses a particularly configured piece of hardware, represented as single fiducial key 10 in FIG. 3A, to orient tracking marker 12 of the monitoring system with regard to the critical area of the surgery. Single fiducial key 10 is attached to a location near the intended surgical area, in the exemplary embodiment of the dental surgical area of FIG. 3A, fiducial key 10 is attached to a dental splint 14. Tracking marker 12 may be connected to fiducial key 10 by tracking pole 11. In embodiments in which the fiducial reference is directly visible to a suitable tracker (see for example FIG. 5 and FIG. 6a) that acquires image information about the surgical site, a tracking marker may be attached directly to the fiducial reference. For example a dental surgery, the dental tracking marker 14 may be used to securely locate the fiducial 10 near the surgical area. The fiducial key 10 may be used as a point of reference, or a fiducial, for the further image processing of data acquired from tracking marker 12 by the tracker.

In other embodiments additional tracking markers 12 may be attached to items independent of the fiducial key 10 and any of its associated tracking poles 11 or tracking markers 12. This allows the independent items to be tracked by the tracker. In some embodiments, the tracker may be a non-stereo optical tracker, for example a camera. The camera may, for example, operate in the visible or near-infrared range.

In a further embodiment at least one of the items or instruments near the surgical site may optionally have a tracker attached to function as tracker for the monitoring system of the invention and to thereby sense the orientation and the position of the tracking marker 12 and of any other additional tracking markers relative to the scan data of the surgical area. By way of example, the tracker attached to an instrument may be a miniature digital camera and it may be attached, for example, to a dentist's drill. Any other markers to be tracked by the tracker attached to the item or instrument must be within the field of view of the tracker.

Using the dental surgery example, the patient is scanned to obtain an initial scan of the surgical site. The particular configuration of single fiducial key 10 allows computer software stored in memory and executed in a suitable controller, for example processor 214 and memory 217 of computer 210 of FIG. 2, to recognize its relative position within the surgical site from the scan data, so that further observations may be made with reference to both the location and orientation of fiducial key 10. In some embodiments, the fiducial reference includes a marking that is apparent as a recognizable identifying symbol when scanned. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan, thereby to allow the determination not only of the location of the fiducial reference, but also of its orientation.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments bearing markers both by orientation and position. The model generated by the monitoring system may then be used to check boundary conditions, and in conjunction with the tracker display the arrangement in real time on a suitable display, for example display 224 of FIG. 2.

In one embodiment, the computer system has a predetermined knowledge of the physical configuration of fiducial key 10 and examines slices/sections of the scan to locate fiducial key 10. Locating of fiducial key 10 may be on the basis of its distinct shape, or on the basis of distinctive identifying and orienting markings upon the fiducial key or on attachments to the fiducial key 10 as tracking marker 12. Fiducial key 10 may be rendered distinctly visible in the scans through higher imaging contrast by the employ of radio-opaque materials or high-density materials in the construction of the fiducial key 10. In other embodiments the material of the distinctive identifying and orienting markings may be created using suitable high density or radio-opaque inks or materials.

Once single fiducial key 10 is identified, the location and orientation of the fiducial key 10 is determined from the scan segments, and a point within fiducial key 10 is assigned as the center of the coordinate system. The point so chosen may be chosen arbitrarily, or the choice may be based on some useful criterion. A model is then derived in the form of a transformation matrix to relate the fiducial system, being fiducial key 10 in one particular embodiment, to the coordinate system of the surgical site. The resulting virtual construct may be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

In some embodiments, the monitoring hardware includes a tracking attachment to the fiducial reference. In the embodiment pertaining to dental surgery the tracking attachment to fiducial key 10 is tracking marker 12, which is attached to fiducial key 10 via tracking pole 11. Tracking marker 12 may have a particular identifying pattern. The trackable attachment, for example tracking marker 12, and even associated tracking pole 11 may have known configurations so that observational data from tracking pole 11 and/or tracking marker 12 may be precisely mapped to the coordinate system, and thus progress of the surgical procedure may be monitored and recorded. For example, as particularly shown in FIG. 3J, single fiducial key 10 may have hole 15 in a predetermined location specially adapted for engagement with insert 17 of tracking pole 11. In such an arrangement, for example, tracking poles 11 may be attached with a low force push into hole 15 of fiducial key 10, and an audible haptic notification may thus be given upon successful completion of the attachment.

It is further possible to reorient the tracking pole during a surgical procedure. Such reorientation may be in order to change the location of the procedure, for example where a dental surgery deals with teeth on the opposite side of the mouth, where a surgeon switches hands, and/or where a second surgeon performs a portion of the procedure. For example, the movement of the tracking pole may trigger a re-registration of the tracking pole with relation to the coordinate system, so that the locations may be accordingly adjusted. Such a re-registration may be automatically initiated when, for example in the case of the dental surgery embodiment, tracking pole 11 with its attached tracking marker 12 are removed from hole 15 of fiducial key 10 and another tracking marker with its associated tracking pole is connected to an alternative hole on fiducial key 10. Additionally, boundary conditions may be implemented in the software so that the user is notified when observational data approaches and/or enters the boundary areas.

In a further embodiment of the system utilizing the invention, a surgical instrument or implement, herein termed a "hand piece" (see FIGS. 5 and 6), may also have a particular configuration that may be located and tracked in the coordinate system and may have suitable tracking markers as described herein. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

Figure 3G:
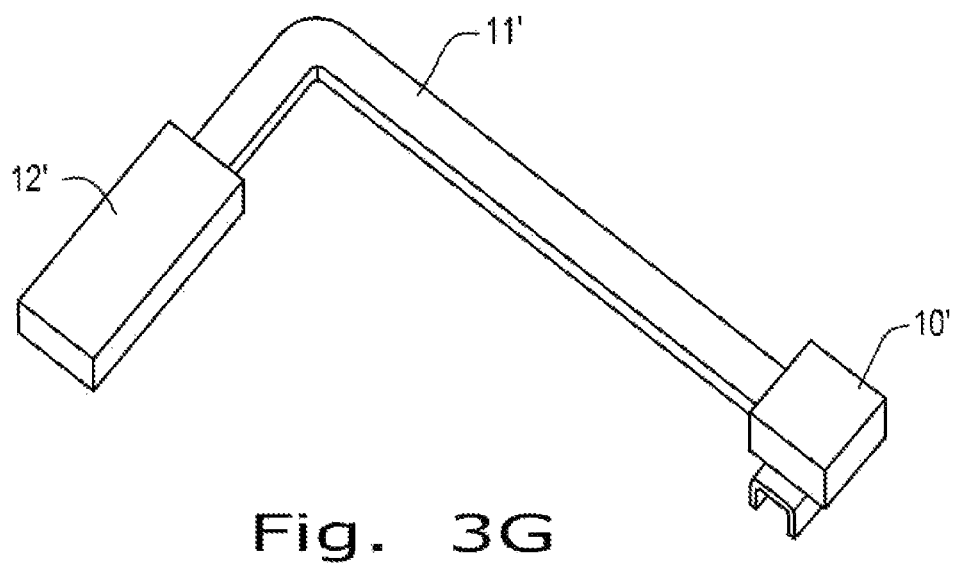
Figure 3H:
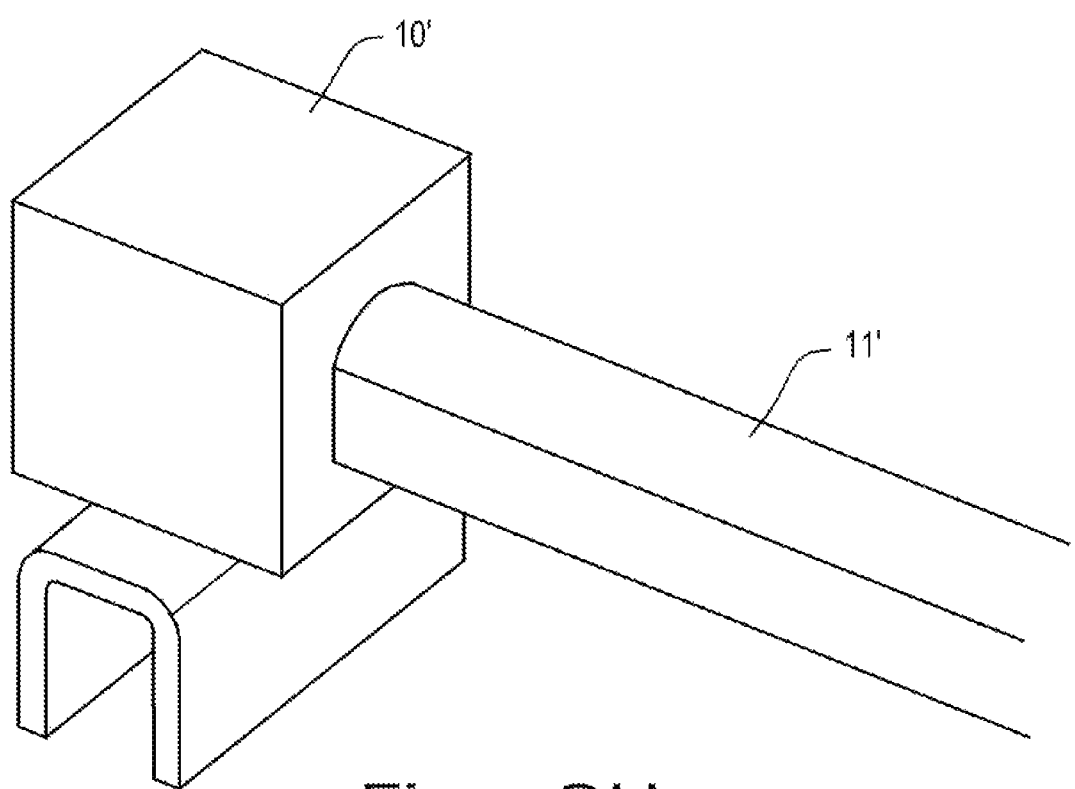
Figure 3I:
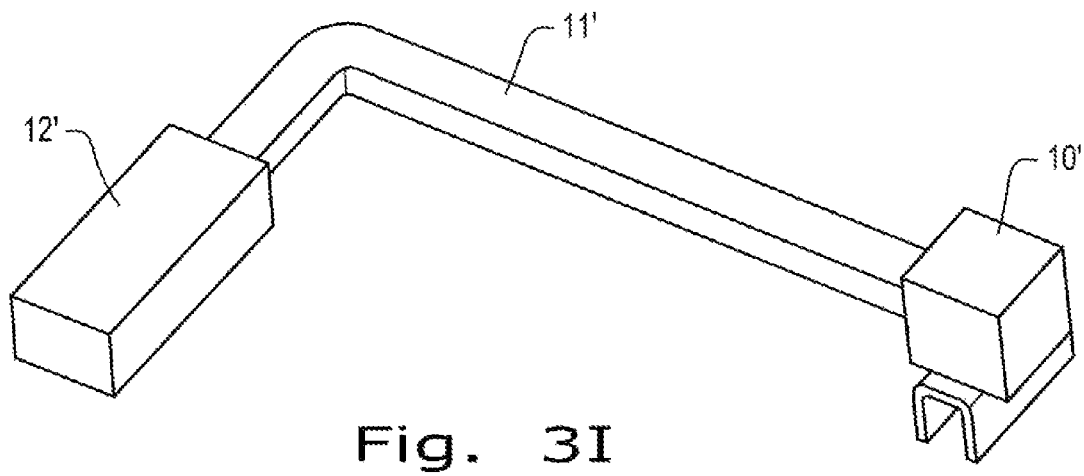
Figure 3J:
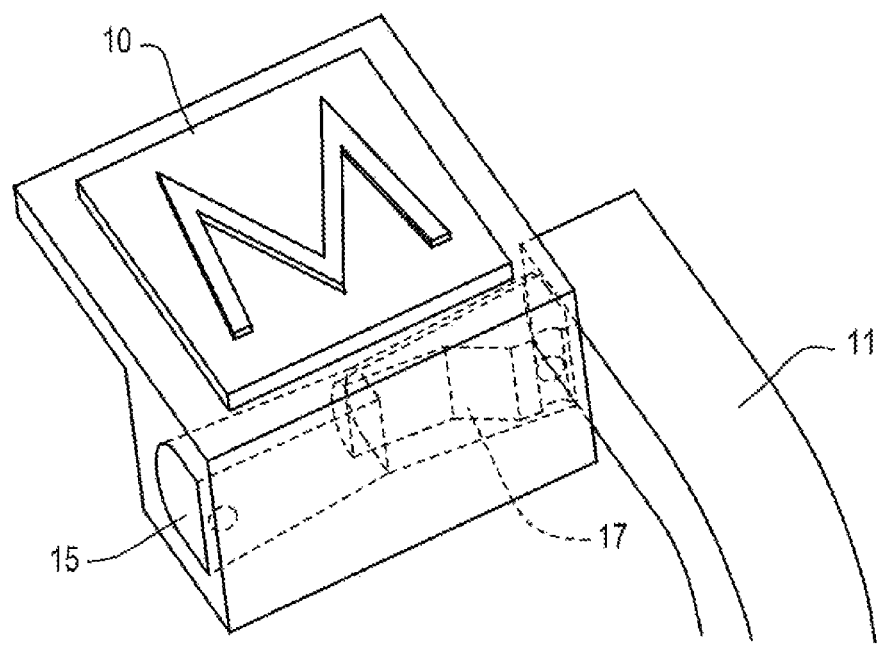

An alternative embodiment of some hardware components are shown in FIGS. 3G-I. Single fiducial key 10' has connection elements with suitable connecting portions to allow a tracking pole 11' to position a tracking marker 12' relative to the surgical site. Conceptually, fiducial key 10' serves as an anchor for pole 11' and tracking marker 12' in much the same way as the earlier embodiment, although it has a distinct shape. The software of the monitoring system is pre-programmed with the configuration of each particularly identified fiducial key, tracking pole, and tracking marker, so that the location calculations are only changed according to the changed configuration parameters.

The materials of the hardware components may vary according to regulatory requirements and practical considerations. Generally, the key or fiducial component is made of generally radio opaque material such that it does not produce noise for the scan, yet creates recognizable contrast on the scanned image so that any identifying pattern associated with it may be recognized. In addition, because it is generally located on the patient, the material should be lightweight and suitable for connection to an apparatus on the patient. For example, in the dental surgery example, the materials of the fiducial key must be suitable for connection to a plastic splint and suitable for connection to a tracking pole. In the surgical example the materials of the fiducial key may be suitable for attachment to the skin or other particular tissue of a patient.

The tracking markers are clearly identified by employing, for example without limitation, high contrast pattern engraving. The materials of the tracking markers are chosen to be capable of resisting damage in autoclave processes and are compatible with rigid, repeatable, and quick connection to a connector structure. The tracking markers and associated tracking poles have the ability to be accommodated at different locations for different surgery locations, and, like the fiducial keys, they should also be relatively lightweight as they will often be resting on or against the patient. The tracking poles must similarly be compatible with autoclave processes and have connectors of a form shared among tracking poles.

The tracker employed in tracking the fiducial keys, tracking poles and tracking markers should be capable of tracking with suitable accuracy objects of a size of the order of 1.5 square centimeters. The tracker may be, by way of example without limitation, a stereo camera or stereo camera pair. While the tracker is generally connected by wire to a computing device to read the sensory input, it may optionally have wireless connectivity to transmit the sensory data to a computing device.

In embodiments that additionally employ a trackable piece of instrumentation, such as a hand piece, tracking markers attached to such a trackable piece of instrumentation may also be light-weight; capable of operating in a 3 object array with 90 degrees relationship; optionally having a high contrast pattern engraving and a rigid, quick mounting mechanism to a standard hand piece.

Figure 4A:
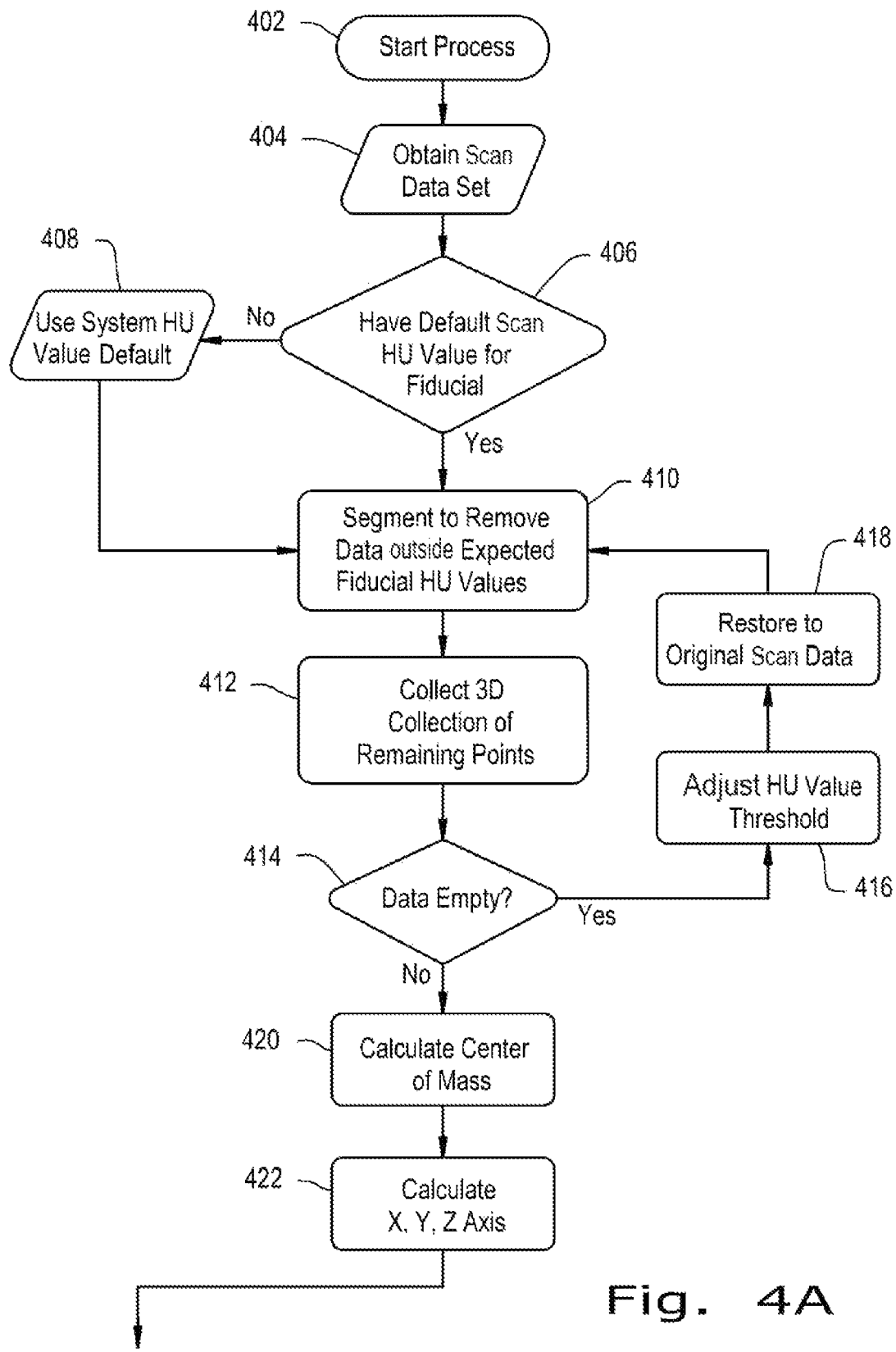
FIGS. 4A-C is a flow chart diagram illustrating one embodiment of the registering method of the present invention.
Figure 4B:
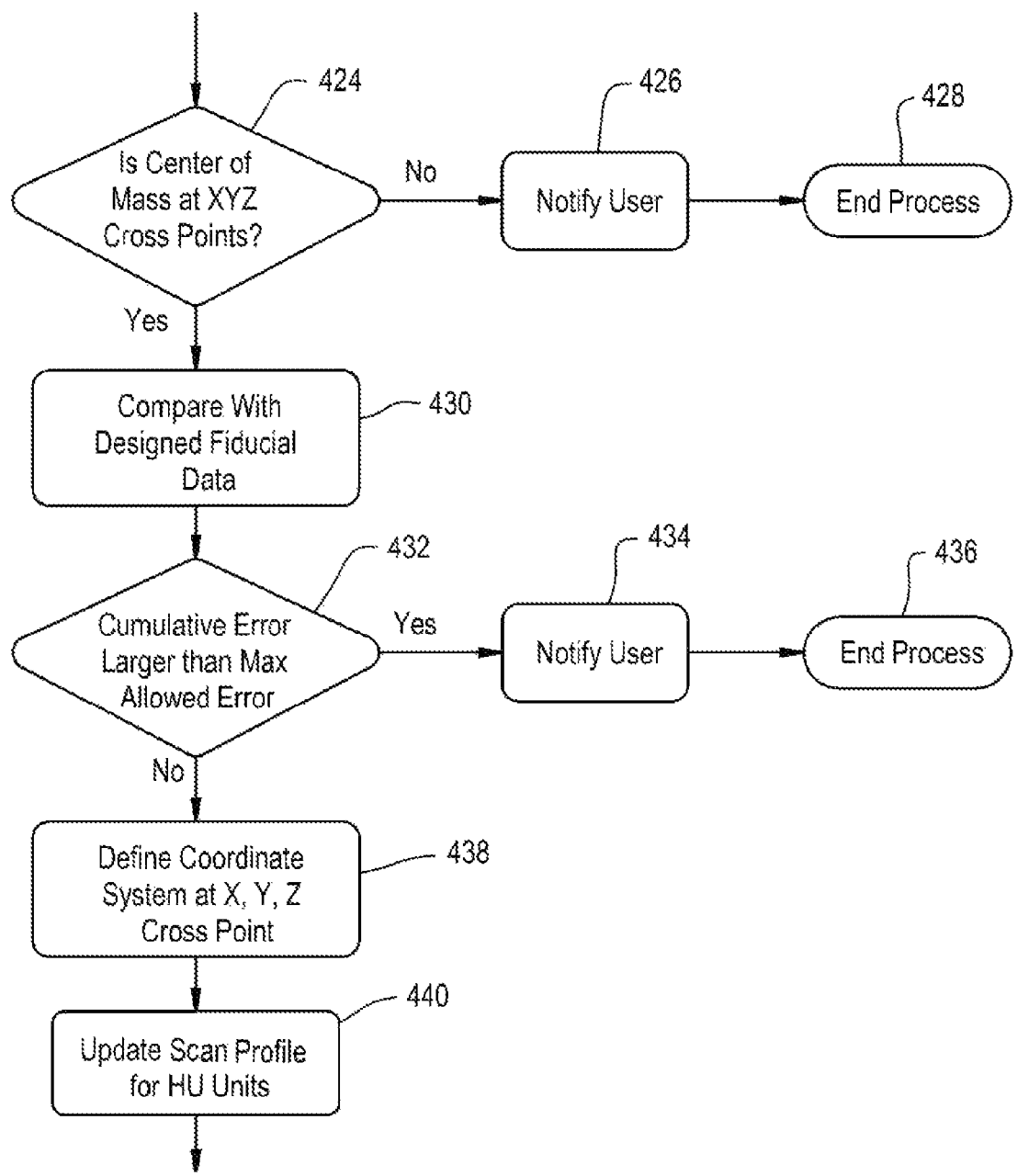
Figure 4C:
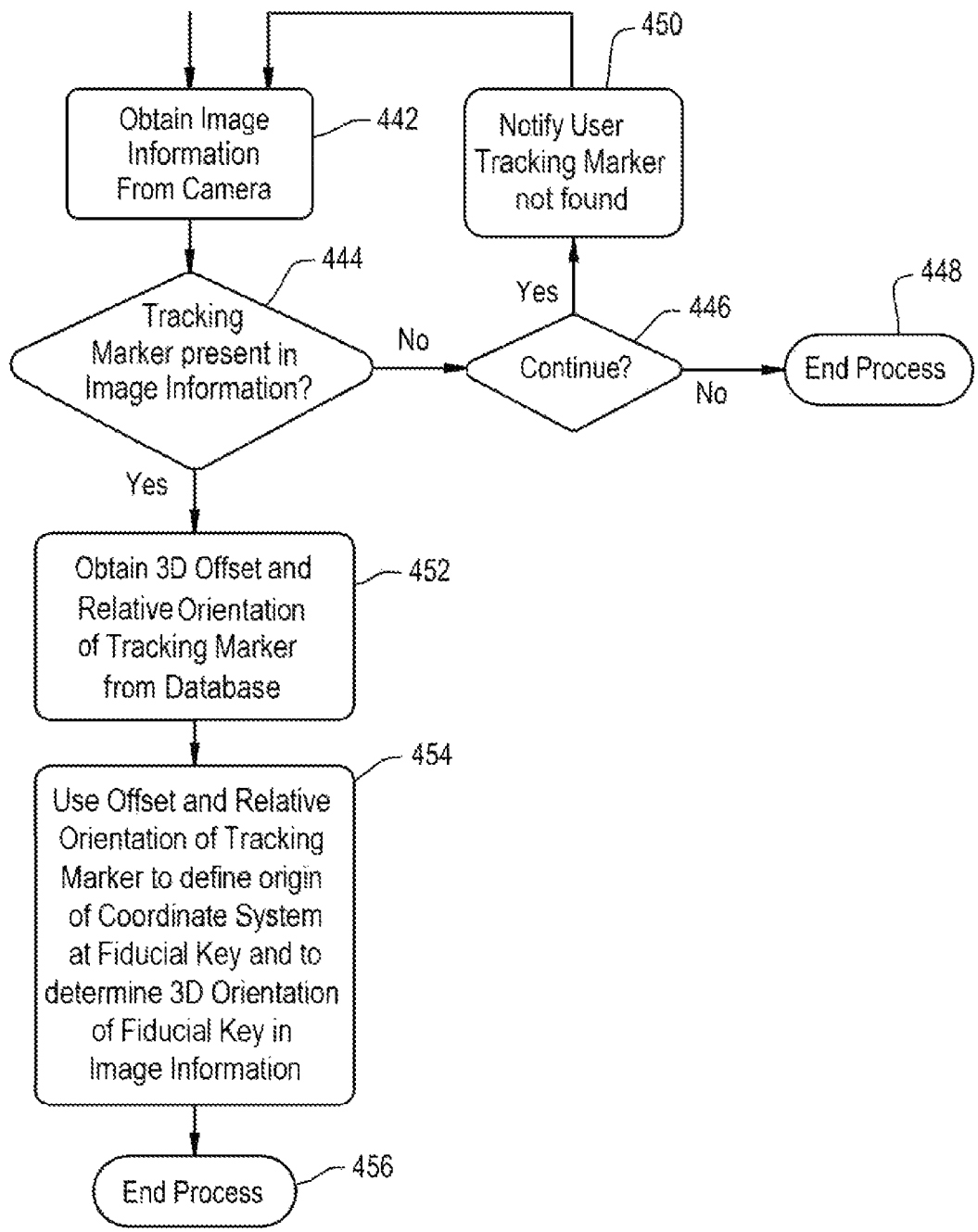

In another aspect of the invention there is presented an automatic registration method for tracking surgical activity, as illustrated in FIGS. 4A-C. FIG. 4A and FIG. 4B together present, without limitation, a flowchart of one method for determining the three-dimensional location and orientation of the fiducial reference from scan data. FIG. 4C presents a flow chart of a method for confirming the presence of a suitable tracking marker in image information obtained by the tracker and determining the three-dimensional location and orientation of the fiducial reference based on the image information.

Once the process starts [402], as described in FIGS. 4A and 4B, the system obtains a scan data set [404] from, for example, a CT scanner and checks for a default CT scan Hounsfield unit (HU) value [at 406] for the fiducial which may or may not have been provided with the scan based on a knowledge of the fiducial and the particular scanner model, and if such a threshold value is not present, then a generalized predetermined default value is employed [408]. Next the data is processed by removing scan segments with Hounsfield data values outside expected values associated with the fiducial key values [at 410], following the collection of the remaining points [at 412]. If the data is empty [at 414], the CT value threshold is adjusted [at 416], the original value restored [at 418], and the segmenting processing scan segments continues [at 410]. Otherwise, with the existing data a center of mass is calculated [at 420], along with calculating the X, Y, and Z axes [at 422]. If the center of mass is not at the cross point of the XYZ axes [at 424], then the user is notified [at 426] and the process stopped [at 428]. If the center of mass is at the XYZ cross point then the data points are compared with the designed fiducial data [430]. If the cumulative error is larger than the maximum allowed error [432] then the user is notified [at 434] and the process ends [at 436]. If not, then the coordinate system is defined at the XYZ cross point [at 438], and the scan profile is updated for the HU units [at 440].

Turning now to FIG. 4C, image information is obtained from the tracker, being a suitable camera or other sensor [442]. The image information is analyzed to determine whether a tracking marker is present in the image information [444]. If not, then the user is queried [446] as to whether the process should continue or not. If not, then the process is ended [448]. If the process is to continue, then the user may be notified that no tracking marker has been found in the image information [450], and the process returns to obtaining image information [442]. If a tracking marker has been found based on the image information, or one has been attached by the user upon the above notification [450], the offset and relative orientation of the tracking marker to the fiducial reference is obtained from a suitable database [452]. The term "database" is used in this specification to describe any source, amount or arrangement of such information, whether organized into a formal multi-element or multi-dimensional database or not. A single data set comprising offset value and relative orientation may suffice in a simple implementation of this embodiment of the invention and may be provided, for example, by the user or may be within a memory unit of the controller or in a separate database or memory.

The offset and relative orientation of the tracking marker is used to define the origin of a coordinate system at the fiducial reference and to determine the three-dimensional orientation of the fiducial reference based on the image information [454] and the registration process ends [458]. In order to monitor the location and orientation of the fiducial reference in real time, the process may be looped back from step [454] to obtain new image information from the camera [442]. A suitable query point may be included to allow the user to terminate the process. Detailed methods for determining orientations and locations of predetermined shapes or marked tracking markers from image data are known to practitioners of the art and will not be dwelt upon here. The coordinate system so derived is then used for tracking the motion of any items bearing tracking markers in the proximity of the surgical site. Other registration systems are also contemplated, for example using current other sensory data rather than the predetermined offset, or having a fiducial with a transmission capacity.

Figure 5:
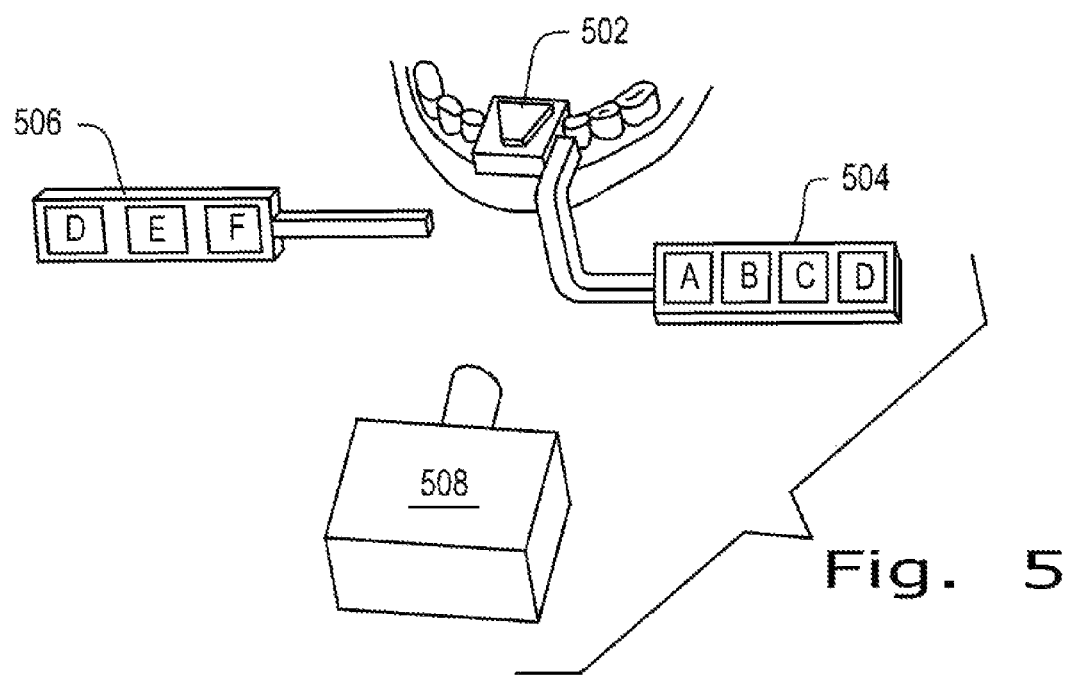
FIG. 5 is a drawing of a dental fiducial key with a tracking pole and a dental drill according to one embodiment of the present invention.

One example of an embodiment of the invention is shown in FIG. 5. In addition to fiducial key 502 mounted at a predetermined tooth and having a rigidly mounted tracking marker 504, an additional instrument or implement 506, for example a hand piece which may be a dental drill, may be observed by a camera 508 serving as tracker of the monitoring system.

Figure 6A:
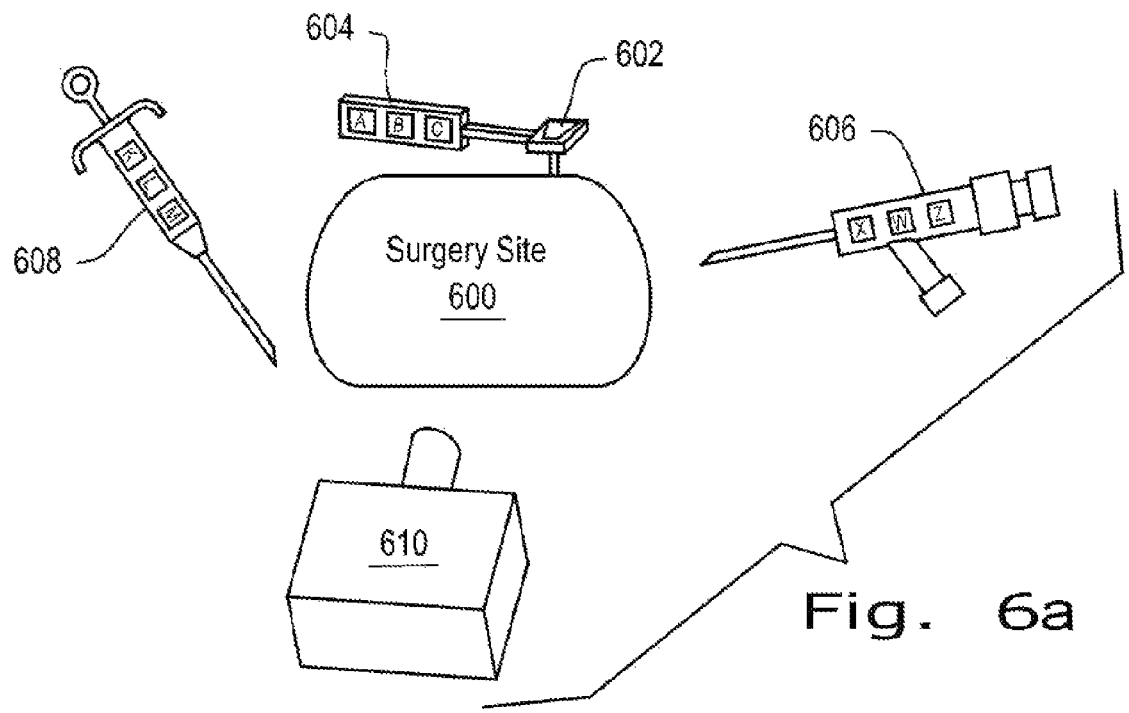
FIG. 6a is a drawing of an endoscopic surgical site showing the fiducial key, endoscope, and biopsy needle according to another embodiment of the invention.

Another example of an embodiment of the invention is shown in FIG. 6a. Surgery site 600, for example a human stomach or chest, may have fiducial key 602 fixed to a predetermined position to support tracking marker 604. Endoscope 606 may have further tracking markers, and biopsy needle 608 may also be present bearing a tracking marker at surgery site 600. Sensor 610, may be for example a camera, infrared sensing device, or RADAR. More particularly, sensor or tracker 610 may be a non-stereo optical tracker.

Having described for greater clarity the invention at the hand of several surgical examples, it bears repeating that it is not limited to the medical field. It is equally applicable to industrial forensics, quality control and product development. It has application in the cutting of gemstones, which may very well be transparent, but the internal failure modes of which may only be revealed by scan techniques. It also may be applied to such comparatively esoteric activities as the restoration and analysis of archaeological bodies, objects and artifacts such as the Antikythera device, or to the investigation of paleontological samples such as dinosaur eggs or specimens that cannot be removed from the embedding rock. It has application wherever the non-visible structure of a body needs to be monitored for position and orientation, such as, for example, while that body is being worked upon.

Figure 6B:
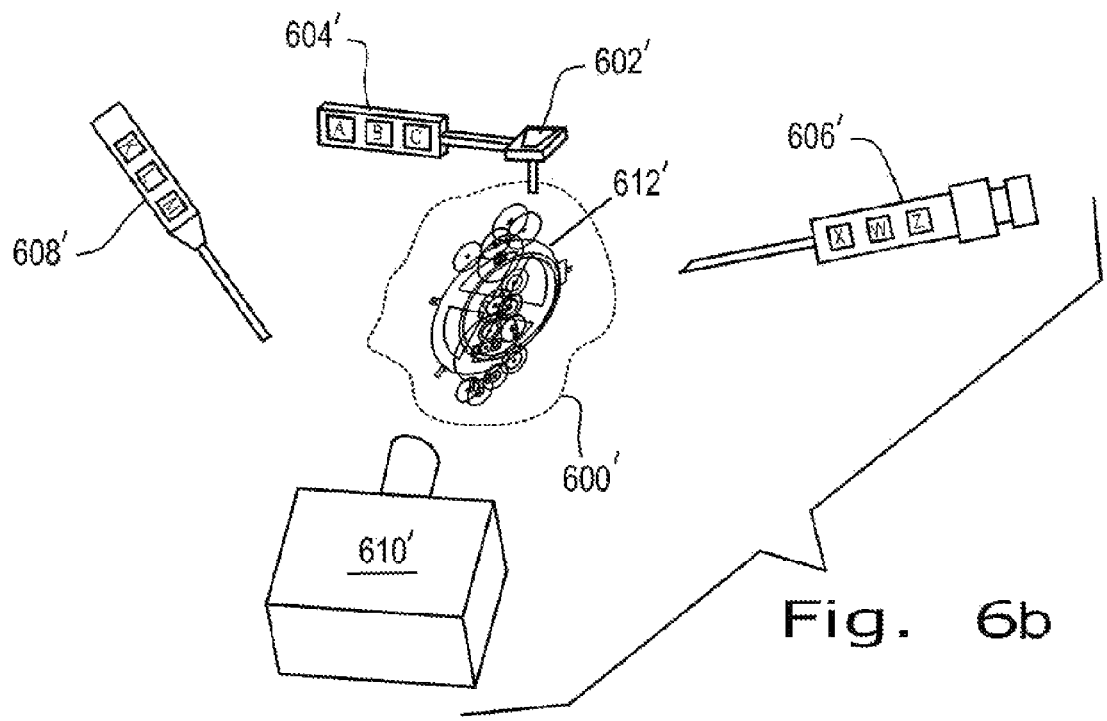
FIG. 6b is a drawing of the monitoring system of the invention as applied to an object having non-visible structure.

In another example, shown in FIG. 6b, the system and method of a further embodiment of the present invention is applied to object 600' that has non-visible internal structure 612'. Object 600' may be, by way of example, an archaeological artifact such as, but not limited to, a artifact that has been encrusted by material over centuries and of which structure 612' has thereby become non-visible. A relevant example object 600' may be a device of historical importance and be fragile and complex, such as the Antikythera device (shown in FIG. 6b). Workers who wish to analyze or restore the device to a museum condition may need to know at every moment of their work exactly how non-visible structure 612' is located and oriented relative to hand pieces 606' and 608'. To this end fiducial reference 602' is attached rigidly at a safe position on object 600', and a scan is made of the object to obtain scan data revealing non-visible structure 612' and showing fiducial reference 602'.

The system and method of the invention of this embodiment proceeds exactly as described above at the hand of the surgical examples. If so required, then, as with the examples above, tracking marker 604' of the type described above may be attached to fiducial reference 602' using a tracking pole (not shown). In other embodiments the tracking marker 604' may belocated directly on fiducial reference 602' itself, as already described. In some embodiments tracking marker 604' may be integral with fiducial reference 602'.

Tracker 610' is arranged to obtain image information about an area encompassing tracking marker 604' associated with fiducial 602'. The example hand pieces 606' and 608' may bear further rigidly attached tracking markers and tracker 610' may be arranged to have a field of view that also encompasses the markers on hand pieces 606' and 608'. The image information obtained by tracker 610' of the region encompassing the fiducial and all the hand pieces to be tracked may then be related to the scan data exhibiting fiducial reference 602' by a controller, for example processor 214 and memory 217 of computer 210 of FIG. 2. The scan data may be predetermined and may reside in memory 217 of the controller 210.

The position and orientation of tracking marker 604' associated with fiducial 602' (irrespective of whether tracking marker 602' be on fiducial 602', integral with fiducial 602', or attached to fiducial 602' by a tracking pole) is then related to the position and orientation of tracking marker 604' as determined from the image information.

The relationship between the position and orientation of fiducial 602' as it appears in the scan data, and the position and orientation of fiducial 602' as determined from the image information is then used to create a spatial transformation matrix that allows the position and orientation of non-visible structure 612' to be determined at any moment in time. With the three-dimensional position and orientation of hand pieces 606' and 608' known from the image information, the three-dimensional position and orientation of the precious and fragile non-visible structure 612' relative to hand pieces 606' and 608' is known at any time. Since the scan has revealed the structural detail of non-visible structure 612', the system and method of this embodiment of the invention provides the user with the ability to know in real time exactly where the hand pieces are moving with respect to such structural detail.

Figure 7A:
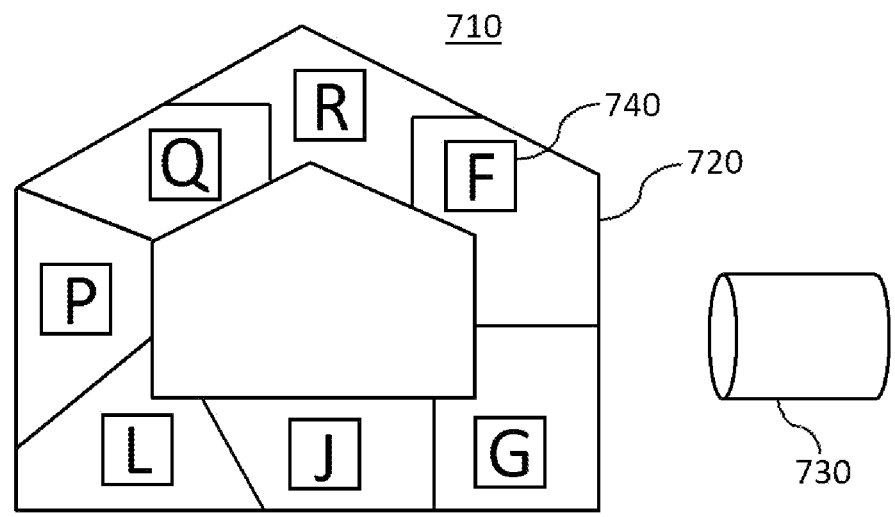
FIGS. 7A and 7B are drawings of a multi-element fiducial pattern comprising a plurality of pattern segments in respectively a default condition and a condition in which the body of a patient has moved to change the mutual spatial relation of the pattern segments.

In another embodiment of the surgical monitoring system of the present invention, shown schematically in FIG. 7A, the fiducial key may comprise a multi-element fiducial pattern 710. In one implementation the multi-element fiducial pattern 710 may be a dissociable pattern. The term "dissociable pattern" is used in this specification to describe a pattern comprising a plurality of pattern segments 720 that topologically fit together to form a contiguous whole pattern, and which may temporarily separated from one another, either in whole or in part. The term "breakable pattern" is used as an alternative term to describe such a dissociable pattern. In other implementations of the invention the segments of the multi-element fiducial pattern 710 do not form a contiguous pattern, but instead their positions and orientations with respect to one another are known when the multi-element fiducial pattern 710 is applied to the surface of the object to be monitored. For example without limitation, it may be applied on the body of the patient near a critical area of a surgical site. In the case of other objects, such as for example object 600' of FIG. 6b, it may be applied on the surface of object 600' proximate a known area of concern to thereby provide greatest local spatial resolution. Each pattern segment 720 is individually locatable based on scan data of the object or a surgical site to which multi-element fiducial pattern 710 may be attached.

Pattern segments 720 are uniquely identifiable by a suitable tracker 730, being differentiated from one another in one or more of a variety of ways. Pattern segments 720 may be mutually differentiable shapes that also allow the identification of their orientations. Pattern segments 720 may be uniquely marked in one or more of a variety of ways, including but not limited to barcoding or orientation-defining symbols. The marking may be directly on the pattern segments 720, or may be on tracking markers 740 attached to pattern segments 720. The marking may be accomplished by a variety of methods, including but not limited to engraving and printing. In the embodiment shown in FIGS. 7A and 7B, by way of non-limiting example, the letters F, G, J, L, P, Q and R have been used.

The materials of the multi-element fiducial pattern 710 and pattern segments 720, and of any tracking markers 740 attached to them, may vary according to regulatory requirements and practical considerations. Generally, the key or fiducial component is made of generally radio opaque material such that it does not produce noise for the scan, yet creates recognizable contrast on the scanned image so that any identifying pattern associated with it may be recognized. The multi-element fiducial pattern 710 and pattern segments 720 may have a distinct coloration difference from the surface to which it is applied. In the particular example of a human patient it may have a distinct coloration difference from human skin in order to be more clearly differentiable by tracker 730. In addition, because it is generally located on the patient or object, the material should be lightweight. The materials may also be capable of resisting damage in autoclave processes such as those employed in the medical environment.

A suitable tracker of any of the types already described is used to locate and image multi-element fiducial pattern 710 within the surgical area. Multi-element fiducial pattern 710 may be rendered distinctly visible in scans of the object to be monitored or surgical area through higher imaging contrast by the employ of radio-opaque materials or high-density materials in the construction of the multi-element fiducial pattern 710. In other embodiments the distinctive identifying and orienting markings on the pattern segments 720 or on the tracking markers 740 may be created using suitable high-density materials or radio-opaque inks, thereby allowing the orientations of pattern segments 720 to be determined based on scan data.

Figure 7B:
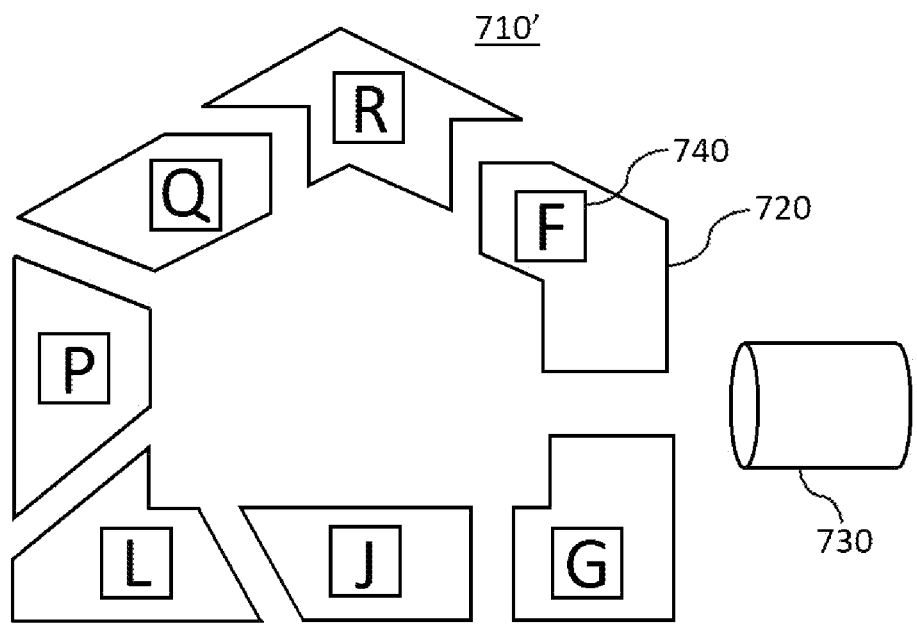

Considering the particular case of surgery, the surgical area may undergo changes in position and orientation. This may occur, for example, as a result of the breathing or movement of the patient. In this process, as shown in FIG. 7B, pattern segments 720 of multi-element fiducial pattern 710 change their relative locations and also, in general, their relative orientations. Information on these changes may be used to gain information on the subcutaneous motion of the body of the patient in the general vicinity of the surgical site by relating the changed positions and orientations of pattern segments 720 to their locations and orientations in a scan done before surgery. In non-surgical applications changes to the object being monitored may similarly occur and internal structure may change in the vicinity of the pattern segments 720.

Using abdominal surgery as example, the patient is scanned, for example without limitation by an x-ray, magnetic resonance imaging (MRI), computerized tomography (CT), or cone beam computerized tomography (CBCT), to obtain an initial image of the surgical site. The particular configuration of multi-element fiducial pattern 710 allows computer software to recognize its relative position within the scan and the image information, so that further observations may be made with reference to both the location and orientation of multi-element fiducial pattern 710. In fact, the computer software may create a coordinate system for organizing objects in the scan. In the case of surgery this may include skin, organs, bones, and other tissue, other surgical instruments bearing suitable tracking markers, and segments 720 of multi-element fiducial pattern 710 etc.

In one embodiment, the computer system has a predetermined knowledge of the configuration of multi-element fiducial pattern 710 and examines slices of a scan of the surgical site to locate pattern segments 720 of multi-element fiducial pattern 710 based on one or more of the radio-opacity density of the material of the pattern segments 720, their shapes and their unique tracking markers 740. Once the locations and orientations of the pattern segments 720 have been determined, a point within or near multi-element fiducial pattern 710 is assigned as the center of the coordinate system. The point so chosen may be chosen arbitrarily, or the choice may be based on some useful criterion. A transformation matrix is derived to relate multi-element fiducial pattern 710 to the coordinate system of the surgical site or object being monitored. In the case of surgical examples the resulting virtual construct may then be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

Considering again the example of abdominal surgery, multi-element fiducial pattern 710 changes its shape as the body moves during surgery. The relative locations and relative orientations of pattern segments 720 change in the process (see FIG. 7A relative to FIG. 7B). In this process the integrity of individual pattern segments 720 is maintained and they may be tracked by tracker 730, including but not limited to a stereo video camera. The changed multi-element fiducial pattern 710' may be compared with initial multi-element fiducial pattern 710' to create a transformation matrix. The relocating and reorienting of pattern segments 720 may therefore be mapped on a continuous basis within the coordinate system of the surgical site. In FIGS. 7A and 7B a total of seven pattern segments 720 are shown. In other embodiments multi-element fiducial pattern 710 may comprise larger or smaller numbers of pattern segments 720. During operation of the surgical monitoring system of this embodiment of the present invention a selection of pattern segments 720 may be employed and there is no limitation that all pattern segments 720 of multi-element fiducial pattern 710 have to be employed. The decision as to how many pattern segments 720 to employ may, by way of example, be based on the resolution required for the surgery to be done or on the processing speed of the controller, which may be, for example, computer 210 of FIG. 2.

For the sake of clarity, FIG. 7A employs a dissociable multi-element fiducial pattern. In other embodiments the multi-element fiducial pattern may have a dissociated fiducial pattern, such as that of FIG. 7B, as default. The individual pattern segments 720 then change position as the body of the patient changes shape near the surgical site during the surgery. In yet other embodiments tracking markers 740 may be absent and the tracking system may rely on tracking the pattern segments 720 purely on the basis of their unique shapes, which lend themselves to determining orientation due to a lack of a center of symmetry. As already pointed out, in other embodiments the pattern segments 720 are not in general limited to being capable of being joined topologically at their perimeters to form a contiguous surface. Nor is there a particular limitation on the general shape of the multi-element fiducial pattern.

Figure 8A:
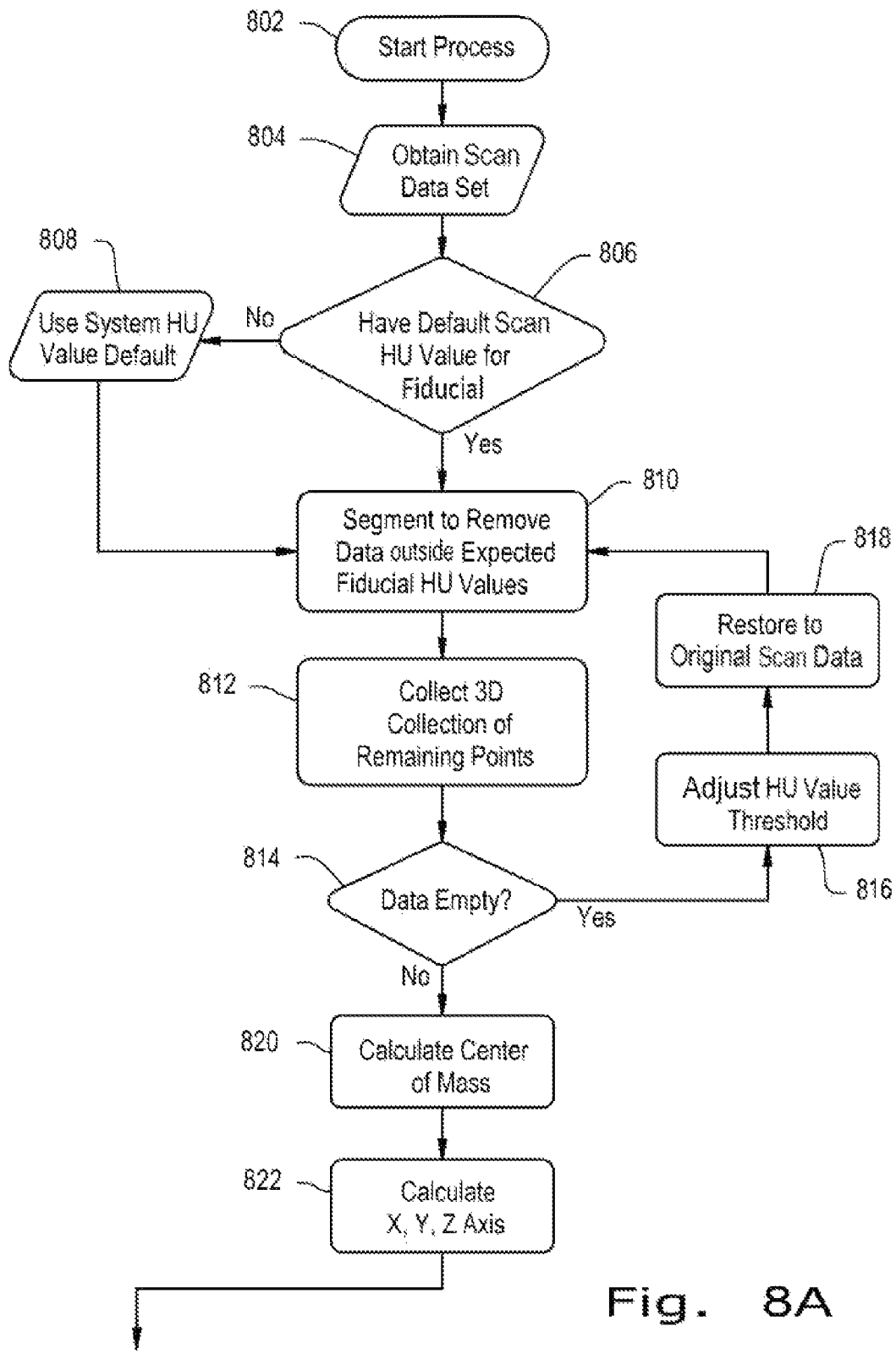
FIGS. 8A-C is a flow chart diagram illustrating one embodiment of the registering method of the present invention as applied to the multi-element fiducial pattern of FIGS. 7A and 7B.
Figure 8B:
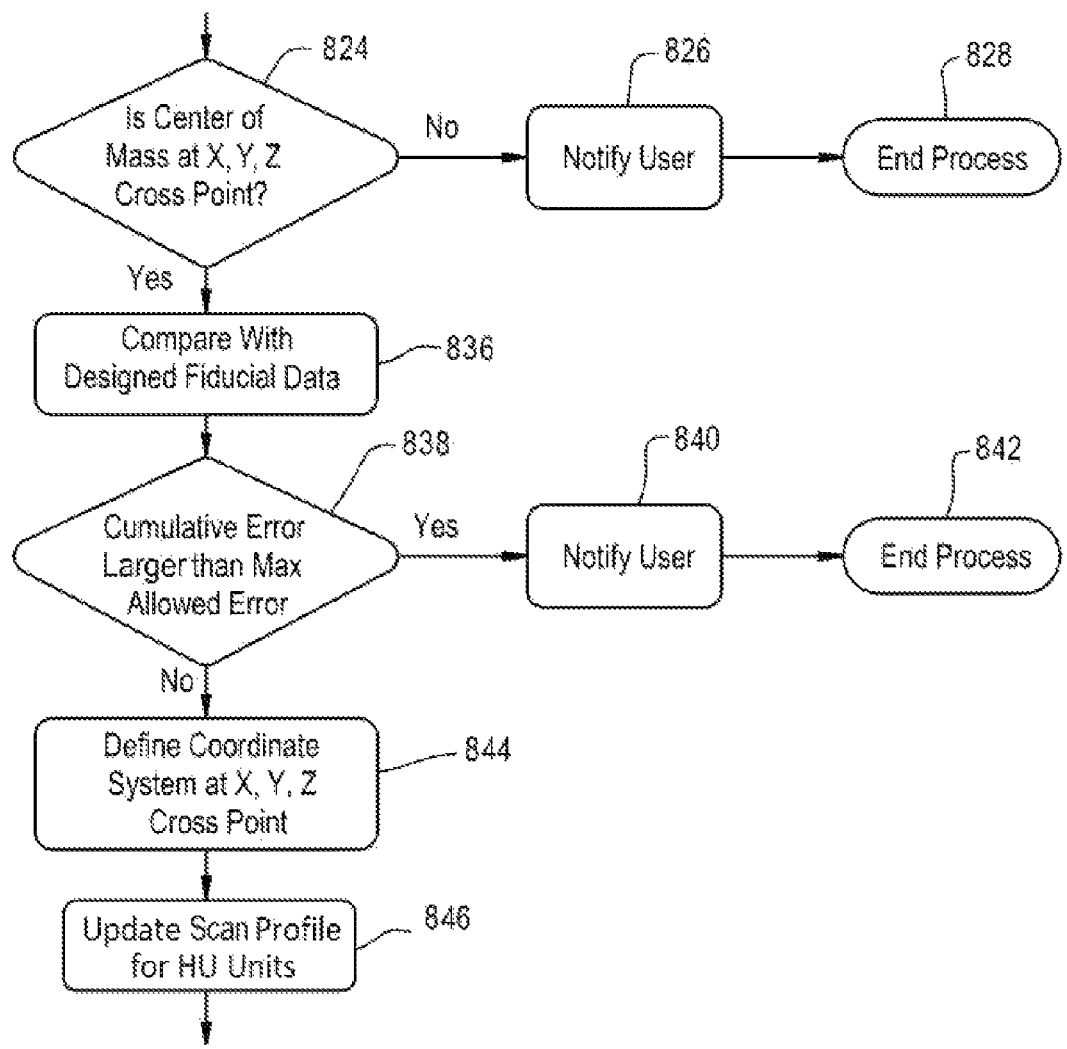
Figure 8C:
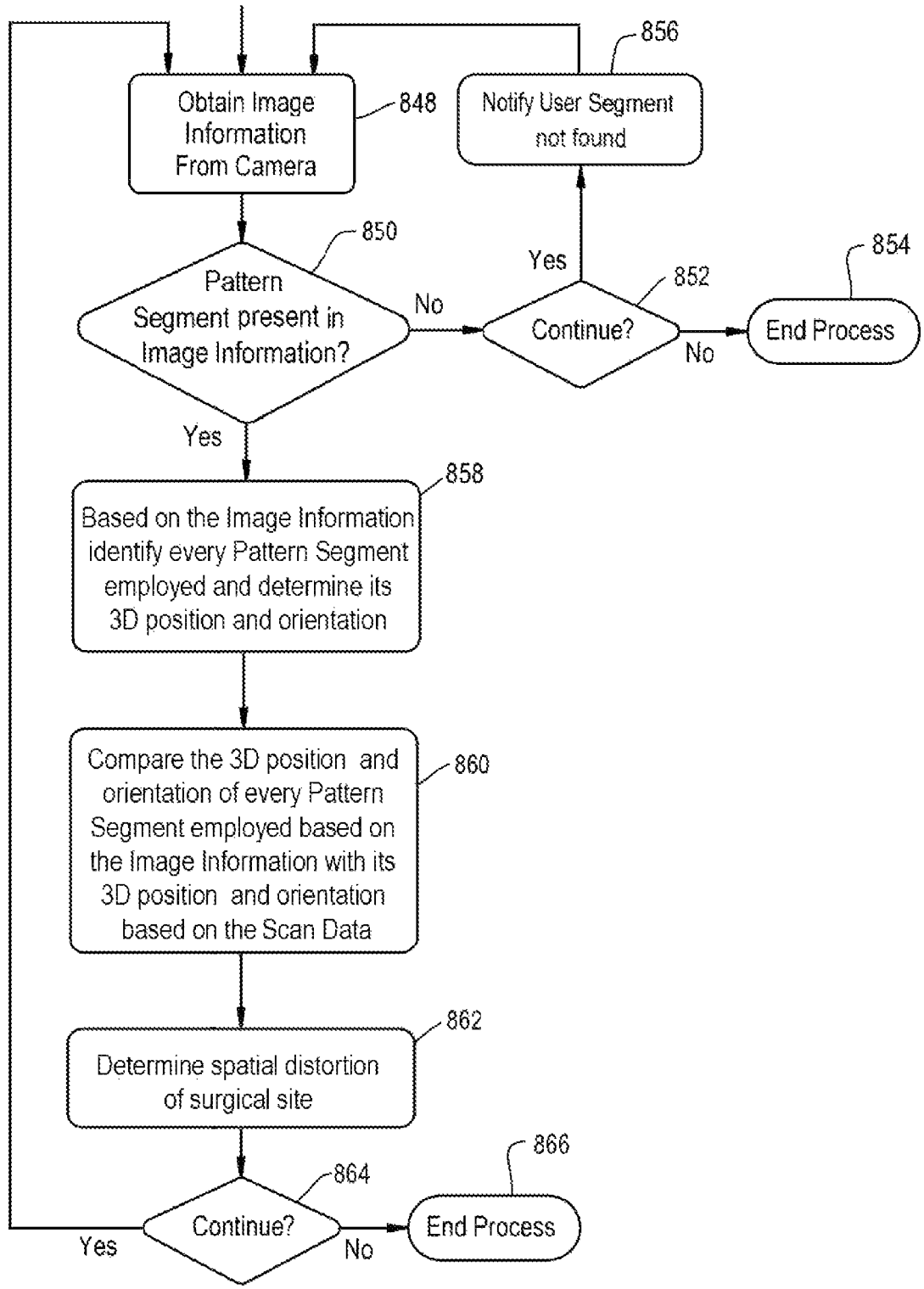

In another aspect of the invention there is presented an automatic registration method for tracking the three-dimensional position and orientation of a body using a multi-element fiducial pattern 710, as shown in the flow chart diagram of FIG. 8A, FIG. 8B and FIG. 8C. FIG. 8A and FIG. 8B together present, without limitation, a flowchart of one method for determining the three-dimensional location and orientation of one segment of multi-element fiducial pattern 710 from scan data. FIG. 8C presents a flow chart of a method for determining the spatial distortion of the body based on the changed orientations and locations of pattern segments 720 of multi-element fiducial pattern 710, using as input the result of applying the method shown in FIG. 8A and FIG. 8B to every one of pattern segments 720 that is to be employed in the determining the spatial distortion of the object in the vicinity of multi-element fiducial pattern 710. In principle, not all pattern segments 720 need to be employed.

Once the process starts [802], as described in FIGS. 8A and 8B, the system obtains a scan data set [804] from, for example, a CT scanner and checks for a default CT scan Hounsfield unit (HU) value [806] for the fiducial, which may or may not have been provided with the scan based on a knowledge of the fiducial and the particular scanner model. If such a default value is not present, then a generalized predetermined system default value is employed [808]. Next the data is processed by removing scan slices or segments with Hounsfield data values outside the expected values associated with the fiducial key [810], followed by the collecting of the remaining points [812]. If the data is empty [814], the CT value threshold is adjusted [816], the original data restored [818], and the processing of scan slices continues [810]. Otherwise, with the existing data a center of mass is calculated [820], as are the X, Y and Z axes [822]. If the center of mass is not at the X, Y, Z cross point [824], then the user is notified [826] and the process ended [828]. If the center of mass is at the X, Y, Z cross point [824], then the pattern of the fiducial is compared to the data [836], and if the cumulative error is larger than the maximum allowed error [838] the user is notified [840] and the process is ended [842]. If the cumulative error is not larger than the maximum allowed error [838], then the coordinate system is defined at the XYZ cross-point [844] and the CT profile is updated for HU units [846]. This process of FIG. 8A and FIG. 8B is repeated for every one of the pattern segments 720 that is to be employed in determining the local spatial distortion of the body. The information on the location and orientation of every one of pattern segments 720 is then used as input to the method described at the hand of FIG. 8C.

Turning now to FIG. 8C, image information is obtained from the camera and it is determined whether any particular segment 720 of the multi-element fiducial pattern 710 on the body is present in the image information [850]. If no particular segment 720 is present in the image information, then the user is queried as to whether the process should continue [852]. If not, then the process is ended [854]. If the process is to continue, the user is notified that no particular segment 720 was found in the image information [856] and the process returns to obtaining image information from the camera [848]. If one of the particular segments 720 is present in the image information at step [850], then, every other pattern segment 720 employed is identified and the three-dimensional location and orientation of all segments 720 employed are determined based on the image information [858]. The three-dimensional location and orientation of every pattern segment employed based on the image information is compared with the three dimensional location and orientation of the same pattern segment as based on the scan data [860]. Based on this comparison the spatial distortion of body is determined [862]. In order to monitor such distortions in real time, the process may be looped back to obtain image information from the camera [848]. A suitable query point [864] may be included to allow the user to terminate the process [866]. Detailed methods for determining orientations and locations of predetermined shapes or marked tracking markers from image data are known to practitioners of the art and will not be dwelt upon here.

By the above method the software of the controller, for example computer 210 of FIG. 2, is capable of recognizing multi-element fiducial pattern 710 and calculating a model of the object or surgical site based on the identity of multi-element fiducial pattern 710 and its changes in shape based on the observation data received from multi-element fiducial pattern 710. This allows the calculation in real time of the locations and orientations of features, such as anatomical features, in the proximity of the multi-element fiducial pattern 710.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A system for monitoring the position and orientation of non-visible structure of a body, the system comprising:
    A multi-element fiducial reference adapted to be rigidly attached to the body, the multi-element fiducial reference comprising a plurality of pattern segments individually locatable based on scan data;
    a three-dimensional tracking marker rigidly attached at a predetermined location in a predetermined orientation on an implement proximate the body;
    a tracker arranged to obtain image information about an area encompassing the multi-element fiducial reference and the marker;
    a computer system coupled to the tracker and having a previously obtained scan data of the body with the fiducial reference fixed to the body and including a processor with memory and a software program having a series of instructions for execution by the processor to determine the relative positions and orientations of the at least a selection of the pattern segments, the marker and the fiducial reference based on the image information and the scan data scan data; and
    a display system in communication with the computer system;
    wherein the system is characterized by at least one of the marker and the tracker being connected to the fiducial reference in a fixed relative position and orientation, the computer system also having software enabling deriving in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data.

2. A system for monitoring the position and orientation of non-visible structure of a body, the system comprising:
  a multi-element fiducial reference capable of being attached to the body, the multi-element fiducial reference being perceptible in scan data of the body, the multi-element fiducial reference comprising a plurality of pattern segments individually locatable based on scan data;
  a three-dimensional tracking marker having a fixed connection with the fiducial reference;
  a tracker having sensory equipment for obtaining image information of a region encompassing the tracking marker and at least a portion of the pattern segments;
  a computing device in communication with the tracker, the computing device having software capable of recognizing the fiducial reference in the scan data and in the image information and calculating a model of the region based on the scan data, the identity of the fiducial reference, and the image information, the model including in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data.

3. A system for monitoring the position and orientation of non-visible structure of a body, the system comprising:
  a tracker for obtaining image information of an area encompassing the body;
  a multi-element fiducial reference configured for removably attaching to the body to be observable by the tracker, the multi-element fiducial reference comprising a plurality of pattern segments individually locatable based on scan data;
  a controller configured to spatially relate the image information to previously obtained scan data of the body with the fiducial reference attached to the body; and
  software executable by the controller to determine a three-dimensional location and orientation of the fiducial reference by relating the image information to the scan data and to derive in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data.

4. The system of claim 3, characterized by at least a selection of the multi-element fiducial reference being at least one of marked and shaped for having at least one of its location and its orientation determined from the scan data.

5. The system of claim 3, characterized in that at least a selection of the multi-element fiducial reference is at least one of marked and shaped to allow the fiducial reference to be uniquely identified from the scan data.

6. The system of claim 3, characterized by a tracking marker in fixed three-dimensional spatial relationship with the fiducial reference, wherein the tracking marker is configured for having at least one of its location and its orientation determined by the controller based on the image information and the scan data.

7. The system of claim 6, characterized by the tracking marker being configured to be removably and rigidly connected to the fiducial reference by a first tracking pole.

8. The system of claim 7, characterized in that the first tracking pole has a three-dimensional structure uniquely identifiable by the controller from the image information.

9. The system of claim 7, characterized in that the first tracking pole has a three-dimensional structure allowing for the three-dimensional orientation of the tracking pole to be determined by the controller from image information.

10. The system of claim 7, characterized in that the first tracking pole and fiducial reference are configured to allow the first tracking pole to connect to a single unique location on the fiducial reference in a first single unique three-dimensional orientation.

11. The system of claim 7, characterized in that the fiducial reference is configured for the attachment in a single second unique three-dimensional orientation of at least a second tracking pole attached to a second tracking marker.

12. The system of claim 6, characterized in that the tracking marker has a three-dimensional shape uniquely identifiable by the controller from image information.

13. The system of claim 6, characterized in that the tracking marker has a three-dimensional shape that allows the three-dimensional orientation of the tracking marker to be determined by the controller from image information.

14. The system of claim 6, characterized in that the tracking marker has a marking uniquely identifiable by the controller and the marking is configured for allowing at least one of its location and its orientation to be determined by the controller based on the image information and the scan data.

15. The system of claim 3, characterized in that every segment of the pattern segments is individually configured for having a segmental three-dimensional location and orientation determinable based on scan data of the surgical site, and for having the segmental three-dimensional location and orientation determinable based on image information about the surgical site.

16. The system of claim 15, wherein the plurality of pattern segments have unique differentiable shapes that allow the controller to identify them uniquely from at least one of scan data and image information.

17. The system of claim 15, further comprising three-dimensional tracking markers attached to at least a selection of the pattern segments, the tracking markers having at least one of identifying marks and orientation marks that allow their three-dimensional orientations to be determined by the controller from the image information.

18. The system of claim 15, wherein the controller is configured for determining the locations and orientations of at least a selection of the pattern segments based on image information and scan data.

19. The system of claim 15, wherein the controller is configured for calculating the locations of anatomical features in the proximity of the multi-element fiducial pattern.

20. The system of claim 3, comprising further tracking markers attached to implements proximate the surgery site, wherein the controller is configured for determining locations and orientations of the implements based on image information and information about the further tracking markers.

21. The surgical monitoring system of claim 3, wherein at least a selection of the multi-element fiducial reference is rigidly and removably attachable to the body.

22. The surgical monitoring system of claim 3, wherein at least a selection of the multi-element fiducial reference is repeatably attachable in the same three-dimensional orientation to the body.

23. A method for relating in real time the three-dimensional position and orientation of non-visible structure of a body to the location and orientation of the structure in a scan of the body, the method comprising:
   removably attaching a multi-element fiducial reference to a fiducial location on the body, the multi-element fiducial reference comprising a plurality of pattern segments individually locatable based on scan data;
   performing a scan with the fiducial reference attached to the fiducial location to obtain scan data encompassing a region with at least a selection of the pattern segments of the multi-element fiducial reference;
   determining the three-dimensional location and orientation of the fiducial reference from the scan data;
   obtaining real time image information of the body;
   determining in real time the three-dimensional location and orientation of the fiducial reference from the image information;
   deriving a spatial transformation matrix for expressing in real time the three-dimensional location and orientation of the fiducial reference as determined from the image information in terms of the three-dimensional location and orientation of the fiducial reference as determined from the scan data; and
   deriving in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data.

24. The method of claim 23, wherein the obtaining real time image information of the surgical site comprises rigidly and removably attaching to at least a selection of the multi-element fiducial reference a first tracking marker in a fixed three-dimensional spatial relationship with the fiducial reference.

25. The method of claim 24, wherein the first tracking marker is configured for having its location and its orientation determined based on image information.

26. The method of claim 24, wherein the attaching the first tracking marker to at least a selection of the multi-element fiducial reference comprises rigidly and removably attaching the first tracking marker to the at least a selection of the multi-element fiducial reference by means of a tracking pole.

27. The method of claim 23, wherein the method further comprises:
   determining the three-dimensional location and orientation of the fiducial reference from scan data comprises determining the three-dimensional location and orientation of at least a selection of the plurality of pattern segments from the scan data; and
   determining in real time the three-dimensional location and orientation of the fiducial reference from the image information comprises determining the three-dimensional location and orientation of the at least a selection of the plurality of pattern segments from image information.

28. A method for tracking in real time changes in a body, the method comprising:
   removably attaching a multi-element fiducial reference to a fiducial location on the body, the multi-element fiducial reference comprising a plurality of pattern segments individually locatable based on scan data;
   performing a scan with the fiducial reference attached to the fiducial location to obtain the scan data;
   determining the three-dimensional locations and orientations of at least a selection of the pattern segments based on the scan data;
   obtaining real time image information of a region encompassing the multi-element fiducial reference;
   determining in real time the three-dimensional locations and orientations of the at least a selection of the pattern segments from the image information; and
   deriving in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data.

29. A method for real time monitoring the three-dimensional position and orientation of an object in relation to a body, the method comprising:
   removably attaching a multi-element fiducial reference to a fiducial location on the body, the multi-element fiducial reference comprising a plurality of pattern segments individually locatable based on scan data;
   performing a scan with the fiducial reference attached to a fiducial location to obtain scan data;
   determining the three-dimensional location and orientation of the fiducial reference from the scan data;
   obtaining real time image information of a region encompassing at least a selection of the pattern segments of the fiducial reference and the object;
   determining in real time the three-dimensional locations and orientations of the at least a selection of the pattern segments of the fiducial reference from the image information;
   deriving a spatial transformation matrix for expressing in real time the three-dimensional location and orientation of the fiducial reference as determined from image information in terms of the three-dimensional location and orientation of the fiducial reference as determined from scan data;
   deriving in real time the spatial distortion of the body proximate the multi-element fiducial reference by comparing in real time the three-dimensional locations and orientations of the at least a selection of the pattern segments as determined from the image information with the three-dimensional locations and orientations of the at least a selection of the pattern segments as determined from the scan data;
   determining in real time the three-dimensional location and orientation of the object from the image information; and
   relating the three-dimensional location and orientation of the object to the three-dimensional location and orientation of the fiducial reference the spatial distortion of the body as determined from the image information.

30. The method of claim 29, wherein determining in real time the three-dimensional location and orientation of the object from the image information comprises rigidly attaching a tracking marker to the object.

31. The method of claim 29, further comprising determining in real time the position and orientation of the object relative to the position and orientation of non-visible structure of the body revealed in the scan.

\* \* \* \* \*